United States Patent
Pellicciari et al.

(10) Patent No.: US 9,777,038 B2
(45) Date of Patent: Oct. 3, 2017

(54) PROCESS FOR PREPARING BILE ACID DERIVATIVES

(71) Applicant: Intercept Pharmaceuticals, Inc., New York, NY (US)

(72) Inventors: Roberto Pellicciari, Perugia (IT); Antimo Gioiello, Perugia (IT)

(73) Assignee: Intercept Pharmaceuticals, Inc., New York, NY (US)

( * ) Notice: Subject to any disclaimer, the term of this patent is extended or adjusted under 35 U.S.C. 154(b) by 0 days.

(21) Appl. No.: 14/438,323

(22) PCT Filed: Oct. 25, 2013

(86) PCT No.: PCT/US2013/066917
§ 371 (c)(1),
(2) Date: Apr. 24, 2015

(87) PCT Pub. No.: WO2014/066819
PCT Pub. Date: May 1, 2014

(65) Prior Publication Data
US 2015/0291653 A1 Oct. 15, 2015

Related U.S. Application Data

(60) Provisional application No. 61/718,966, filed on Oct. 26, 2012.

(51) Int. Cl.
*C07J 31/00* (2006.01)
*C07J 9/00* (2006.01)

(52) U.S. Cl.
CPC .............. *C07J 31/006* (2013.01); *C07J 9/00* (2013.01); *C07J 9/005* (2013.01)

(58) Field of Classification Search
CPC ............. C07J 9/005; C07J 31/006; C07J 9/00
See application file for complete search history.

(56) References Cited

U.S. PATENT DOCUMENTS

| | | | |
|---|---|---|---|
| 5,216,015 A | 6/1993 | McGarry et al. | |
| 7,138,390 B2 | 11/2006 | Pellicciari | |
| 7,812,011 B2 | 10/2010 | Pellicciari | |
| 7,932,244 B2 | 4/2011 | Pellicciari | |
| 2008/0182832 A1 | 7/2008 | Pellicciari | |
| 2011/0172198 A1 | 7/2011 | Pellicciari | |

FOREIGN PATENT DOCUMENTS

WO   WO 2010/036427 A1   4/2010

OTHER PUBLICATIONS

Rizzo et al, Molecular Pharmacology, Functional Characterization of the Semisynthetic Bile Acid Derivative INTW67, a Dual Farnesoid X Receptor and TGR5 Agonist, 2010, 78(4), pp. 617-630.*
Shalon et al, Synthetic Communications, Improved Aldehyde Synthesis: Preparation of 3-alpha, 7-alpha, 1-alpha-Triacetoxy-5 beta-Cholan-23-al with Ruthenium Tetroxide in Neutral Medium, 1973, 3(4), pp. 287-291.*
Rizzo, G., et al., Functional Characterization of the Semisynthetic Bile Acid Derivative INT-767, a Dual Farnesoid X Receptor and TGR5 Agonist, Molecular Pharmacology, 78( 4):617-630 (2010).
Norinder, Jakob et al., "An Enantioselective Route to α-Methyl Carboxylic Acids via Metal and Enzyme Catalysis", *Organic Letters*, vol. 9, No. 24, pp. 5095-5098, 2007.

* cited by examiner

*Primary Examiner* — Paul A Zucker
(74) *Attorney, Agent, or Firm* — Michelle Iwamoto-Fan; Intercept Pharmaceuticals, Inc.

(57) ABSTRACT

The present invention relates to processes for preparing compounds of formula I:

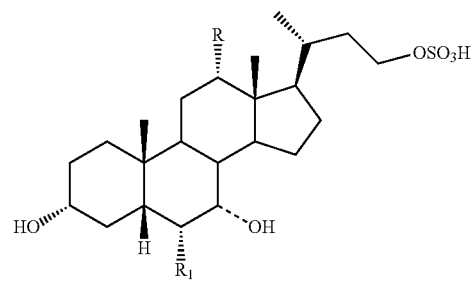

or a pharmaceutically acceptable salt or solvate thereof.

6 Claims, 2 Drawing Sheets

PROCESS FOR PREPARING BILE ACID DERIVATIVES

CROSS-REFERENCE TO RELATED APPLICATION

This application is a national stage application, filed under 35 U.S.C. §371, of International Application No. PCT/US2013/066917, filed on Oct. 25, 2013, which claims priority to, and the benefit of, U.S. application Ser. No. 61/718,966, filed on Oct. 26, 2012, each of which is incorporated herein by reference in its entirety.

SUMMARY OF THE INVENTION

The present invention relates to processes for preparing a compound of formula I:

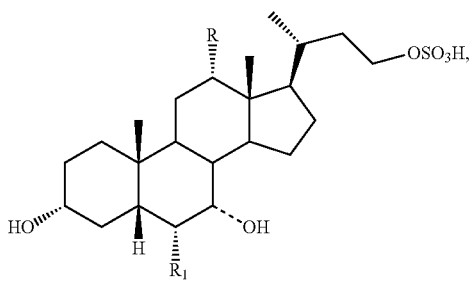

(I)

or a pharmaceutically acceptable salt or solvate thereof, wherein
the dashed bond (----) at position 7 indicates that the substituent is in an α or β stereochemistry;
R is hydrogen or hydroxy; and
$R_1$ is hydrogen or $C_1$-$C_6$ alkyl.

Unless otherwise defined, all technical and scientific terms used herein have the same meaning as commonly understood by one of ordinary skill in the art to which this invention belongs. In the case of conflict, the present specification, including definitions, will control. In the specification, the singular forms also include the plural unless the context clearly dictates otherwise. Although methods and materials similar or equivalent to those described herein can be used in the practice or testing of the present invention, suitable methods and materials are described below. All publications, patent applications, patents, and other references mentioned herein are incorporated by reference. The references cited herein are not admitted to be prior art to the claimed invention. In addition, the materials, methods, and examples are illustrative only and are not intended to be limiting.

Other features and advantages of the invention will be apparent from the following detailed description and claims.

DETAILED DESCRIPTION OF THE INVENTION

Figure 1:
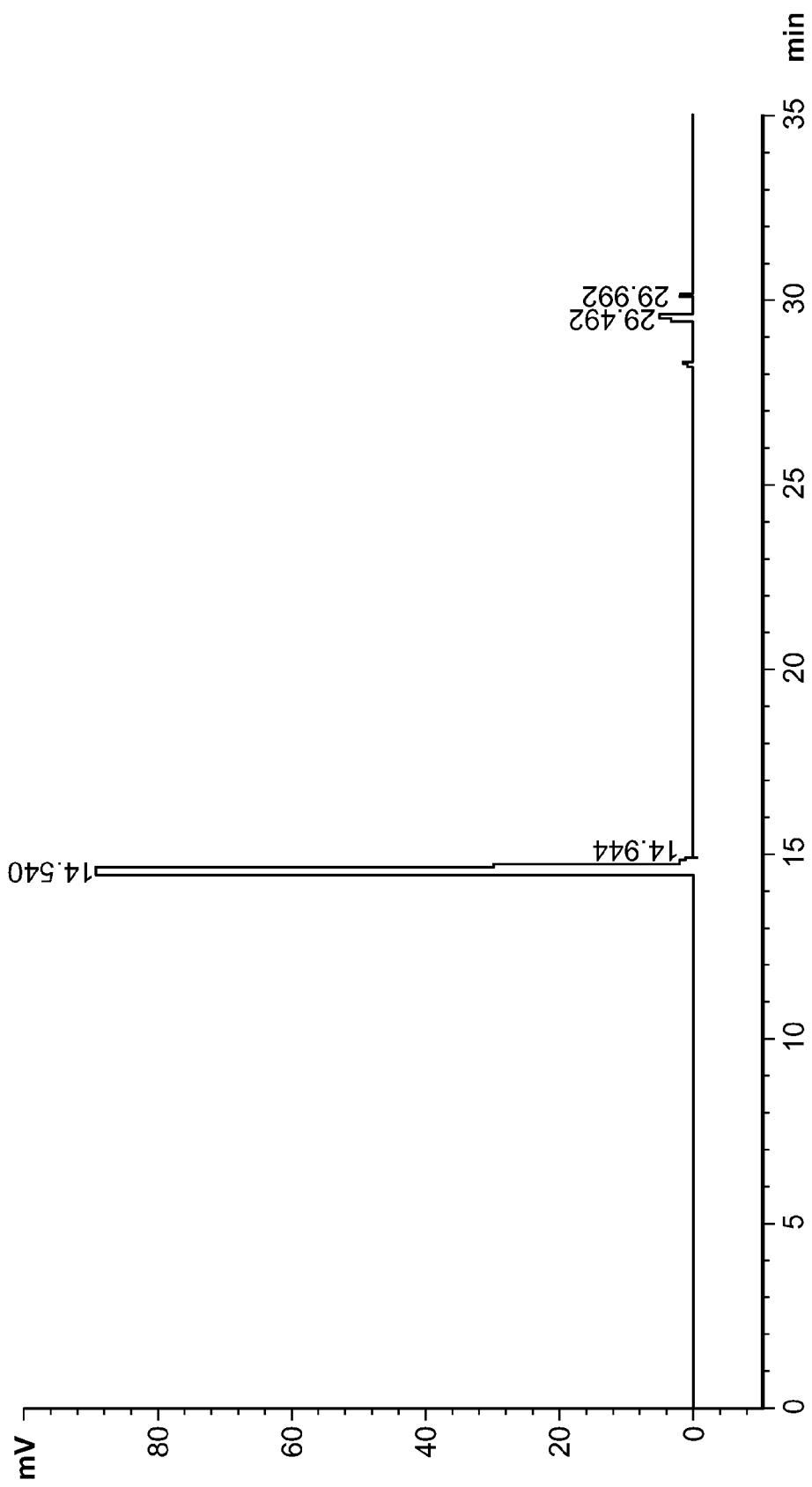
FIG. 1: HPLC chromatogram of compound VIIA obtained from Example 2.

The present invention relates to processes for preparing a compound of formula I:

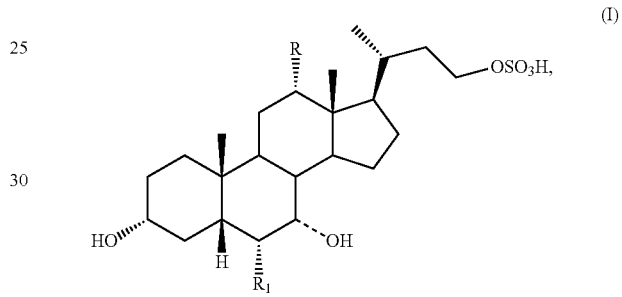

(I)

or a pharmaceutically acceptable salt or solvate thereof, wherein
the dashed bond (----) at position 7 indicates that the substituent is in an α or β stereochemistry;
R is hydrogen or hydroxy; and
$R_1$ is hydrogen or $C_1$-$C_6$ alkyl.

In one aspect, a compound of formula I, or a pharmaceutically acceptable salt or solvate thereof, can be prepared starting from a compound of formula II in a 4-step process. See Scheme 1. The preparation of the starting materials, 6α-ethyl-5β-cholanoic acids, is disclosed in EP 1392714 and EP 1568706.

Scheme 1

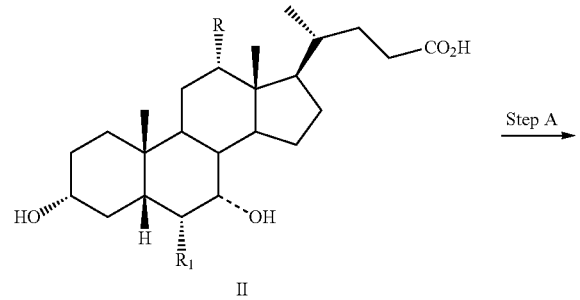

Step A

-continued

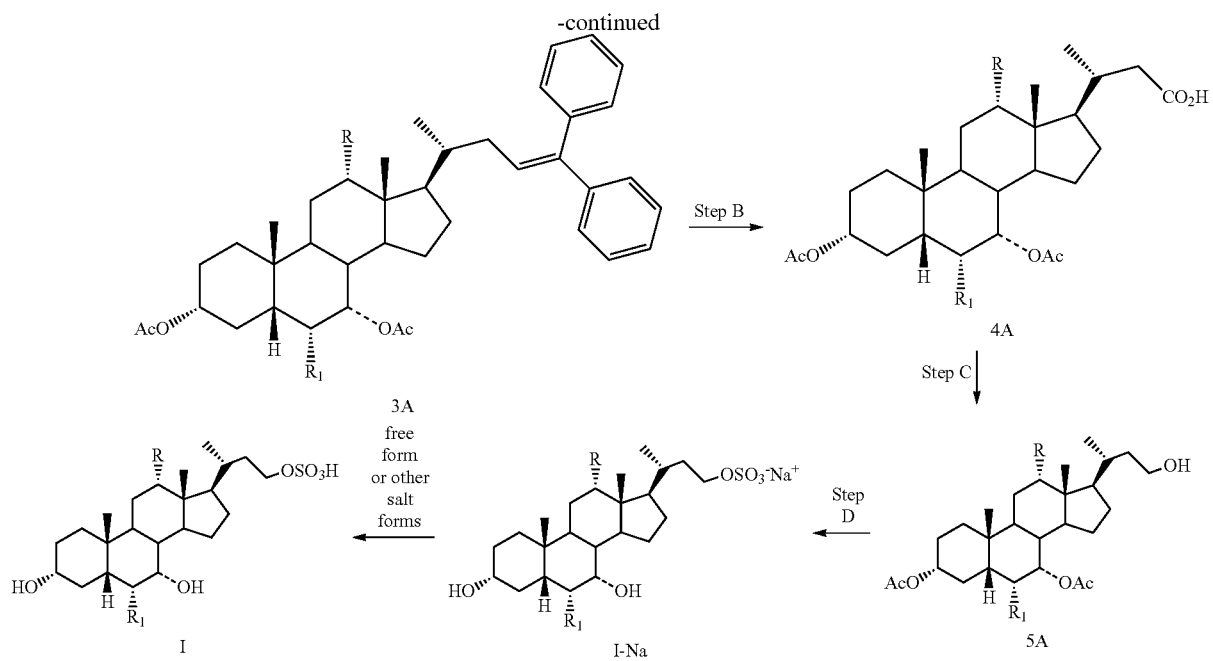

3A

4A

5A

I-Na

I
free form or other salt forms

Step A is the protection of the hydroxy groups at the C3 and C7 positions of a compound of formula II and a Grignard reaction to form a compound of formula 3A. Step B is the oxidative cleavage of the double bond of a compound of formula 3A to give a compound of formula 4A. Step C is the reduction of the C23 carboxylic acid of a compound of formula 4A to afford a compound of formula 5A. Step D is the sulfonation of the C23 hydroxy group of a compound of formula 5A to give a salt of formula I-Na. A salt of formula I-Na can be converted to its free form (i.e., a compound of formula I) or other salt forms (e.g., a salt of formula I-(Et)$_3$NH).

In one aspect, a compound of formula I, or a pharmaceutically acceptable salt or solvate thereof, can be prepared starting from a compound of formula II in a 6-step process. See Scheme 2.

Scheme 2

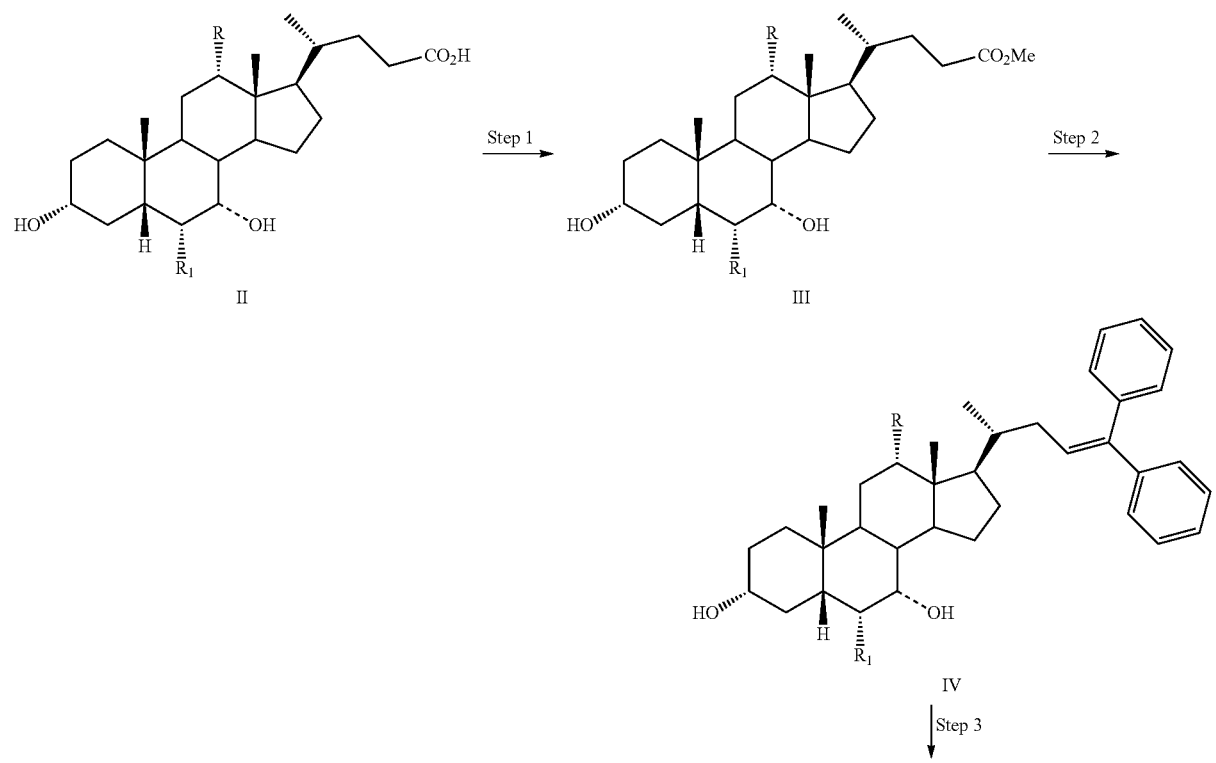

II

III

IV

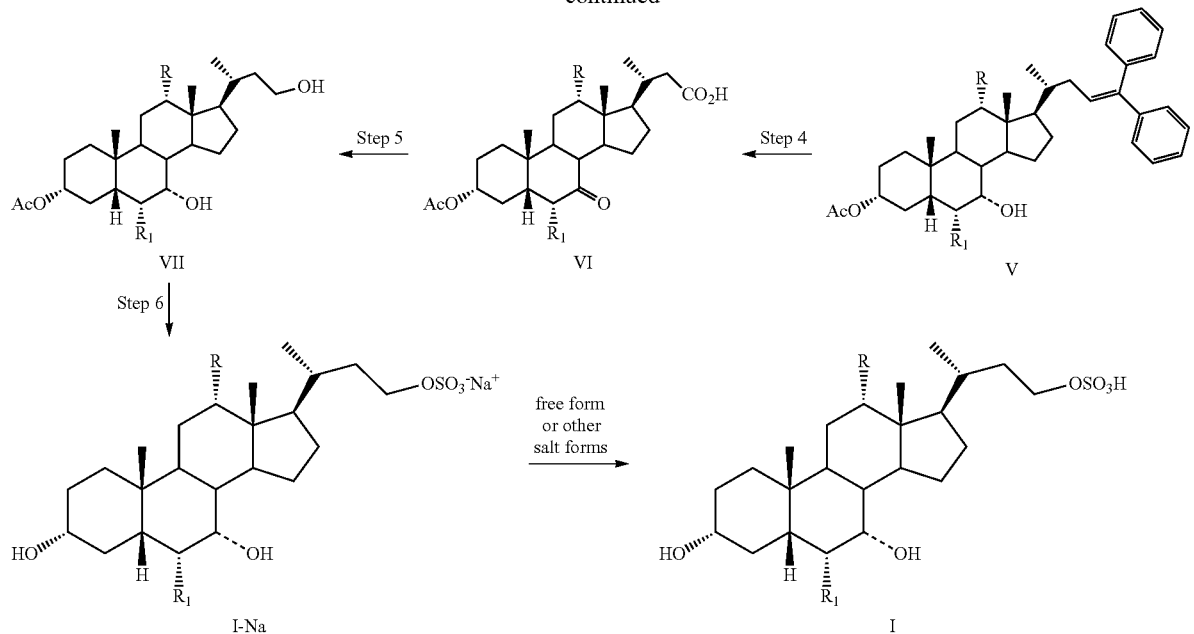

Step 1 is the esterification of a compound of formula II to obtain a compound of formula III. Step 2 is a Grignard reaction to form a compound of formula IV from a compound of formula III. Step 3 is the protection of the hydroxy group at the C3 position of a compound of formula IV to afford a compound of formula V. Step 4 is the oxidative cleavage of the double bond and C7 hydroxy oxidation of a compound of formula V to give a compound of formula VI. Step 5 is the reduction of the C23 carboxylic acid and C7 carbonyl group of a compound of formula VI to afford a compound of formula VII. Step 6 is the sulfonation of the C23 hydroxy group of a compound of formula VII to give a salt of formula I-Na. A salt of formula I-Na can be converted to its free form (i.e., a compound of formula I) or other salt forms (e.g., a salt of formula I -(Et)$_3$NH).

In Scheme 2 step 4, the C7 keto group is formed during the oxidative cleavage (e.g., with ruthenium), which is a competing side reaction. This competing side reaction can be avoided by protecting the C7 hydroxy group along with the C3 hydroxy group in step 3 of Scheme 2 using Ac$_2$O and Bi(OTf)$_3$ in dichloromethane.

A process to synthesize compound IA:

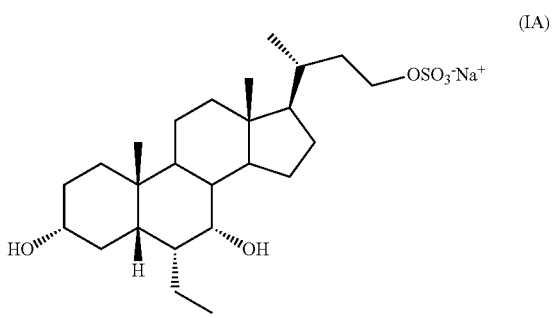

has been disclosed in U.S. Pat. No. 7,932,244 (herein referred to as the '244 patent). See Scheme 3.

Scheme 3

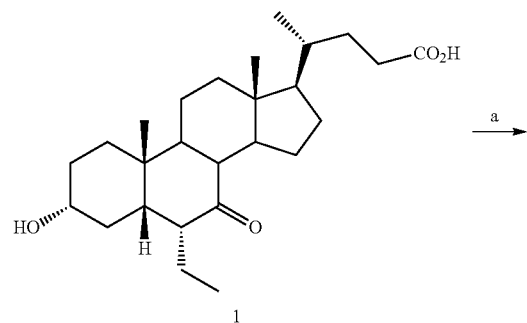

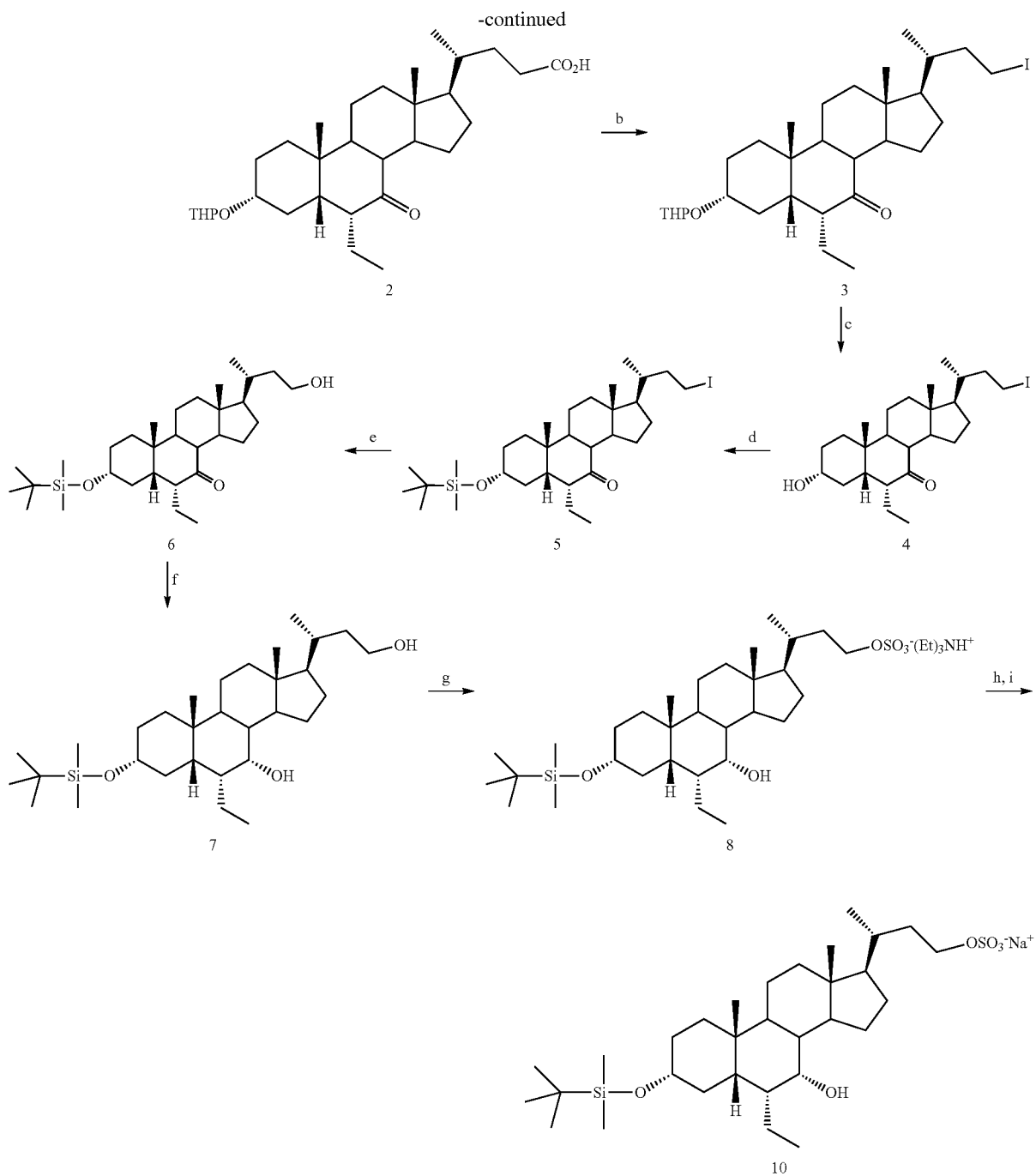

Although compound IA can be prepared by following the process of the '244 patent (corresponds to compound 10 in Scheme 3), a more efficient synthetic route is necessary for the production on a commercial scale. The process of the present invention discloses a more efficient route to generate a compound of formula I (e.g., compound IA) that allows for production on a commercial scale. The process of the present invention (Scheme 1 or Scheme 2) is advantageous to the known process as disclosed in the '244 patent (Scheme 3). The '244 patent discloses an 8-step process whereas the present invention is only a 4-step process according to Scheme 1 or a 6-step process according to Scheme 2. The overall yield of the process of the present invention is at least 46% for compound IA according to Scheme 2 and 45% according to Scheme 1, whereas the yield of the '244 patent is approximately 7%. The present process requires fewer steps and affords a substantially higher yield, which allows for large industrial scale synthesis of a compound of formula I. The process of the present invention utilizes different methodology and different bond breaking and forming steps than those of the '244 patent.

The Process of Scheme 1

In one aspect, the present invention relates to a process for preparing a compound of formula I:

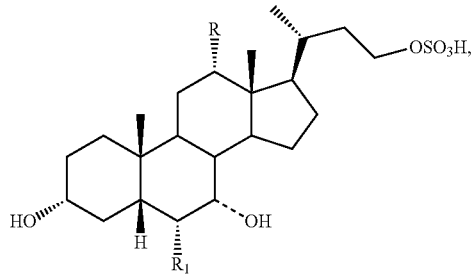

(I)

or a pharmaceutically acceptable salt or solvate thereof, wherein the dashed bond (----) at position 7 indicates that the substituent is in an α or β stereochemistry;

R is hydrogen or hydroxy; and $R_1$ is hydrogen or $C_1$-$C_6$ alkyl, comprising the steps of Step A: converting a compound of formula II to a compound of formula 3A:

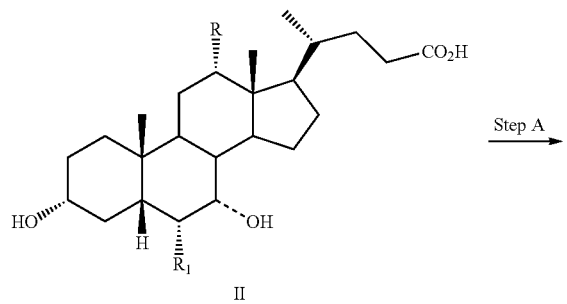

Step B: converting a compound of formula 3A to a compound of formula 4A:

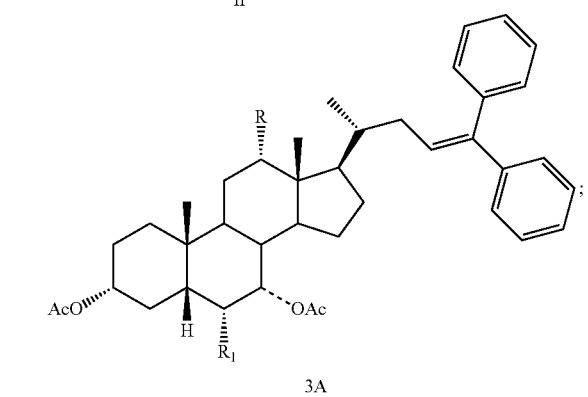

Step C: converting a compound of formula 4A to a compound of formula 5A:

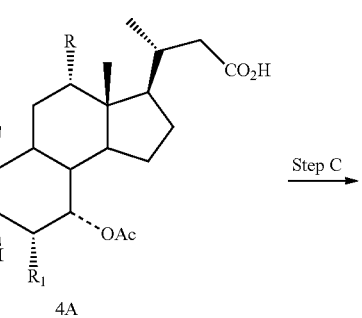

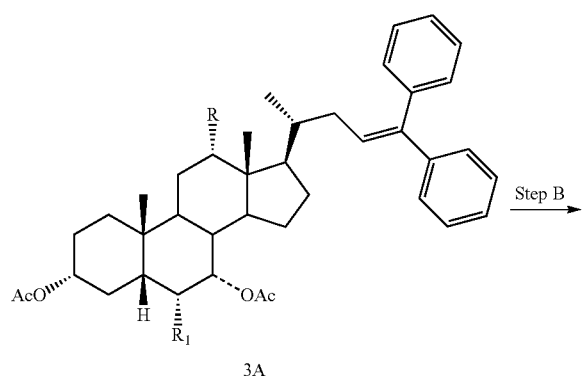

and

Step D: converting a compound of formula 5A to a compound of formula I-Na:

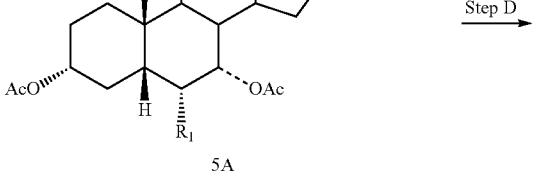

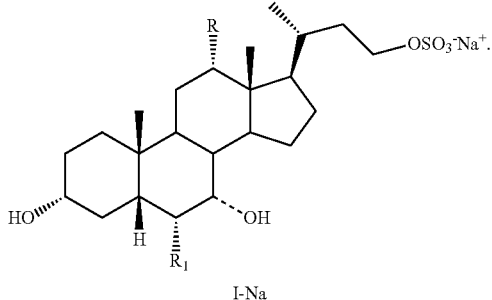

I-Na

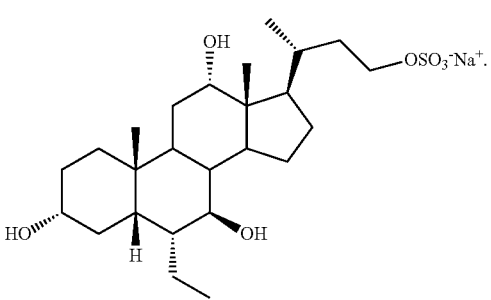
(ID)

In one aspect, the present invention relates to a process for preparing a compound or a pharmaceutically acceptable salt of formula I, wherein R is hydroxy. In another aspect, R is hydrogen. In one aspect, $R_1$ is $C_1$-$C_6$ alkyl. In one aspect, $R_1$ is methyl. In another aspect, $R_1$ is ethyl. In another aspect, $R_1$ is propyl. In another aspect, R is hydrogen and $R_1$ is $C_1$-$C_6$ alkyl. In another aspect, R is hydroxyl and $R_1$ is $C_1$-$C_6$ alkyl. In another aspect, R is hydrogen and $R_1$ is $C_1$-$C_3$ alkyl. In another aspect, R is hydroxyl and $R_1$ is $C_1$-$C_3$ alkyl.

In one aspect, the present invention relates to a process for preparing a compound of formula I or a pharmaceutically acceptable salt or solvate thereof, wherein the salt is selected from

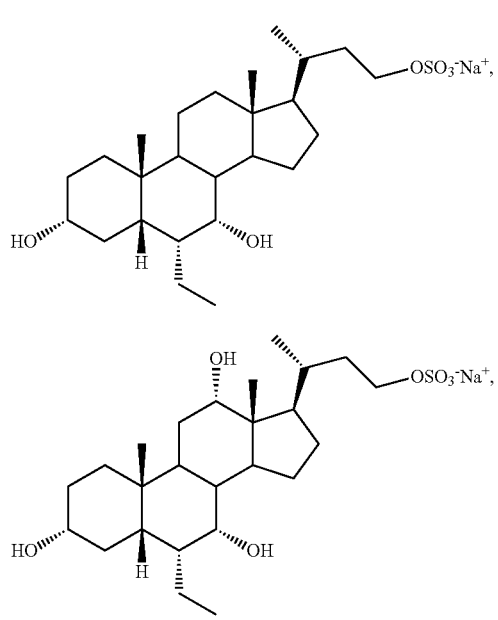

In one aspect, the present invention relates to a process for preparing a compound of formula I or a pharmaceutically acceptable salt or solvate thereof, wherein the salt is selected from

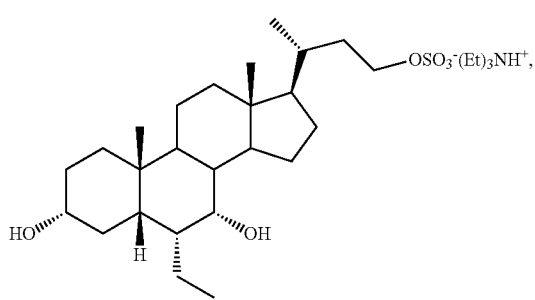
(IAA)

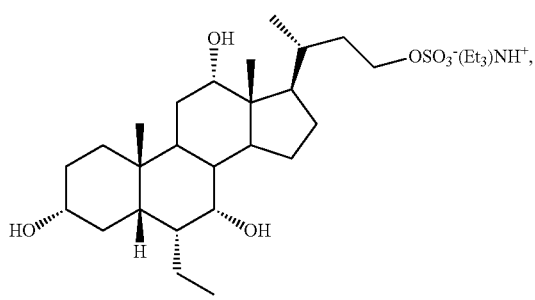
(IBB)

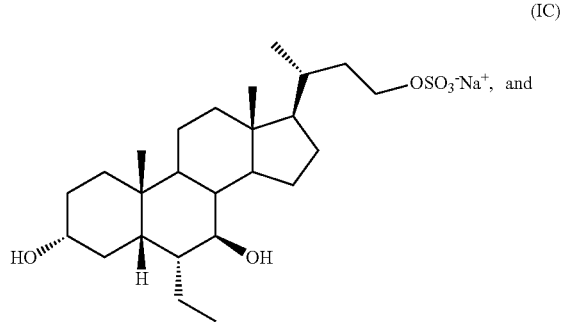
(ICC)

13

-continued (IDD)

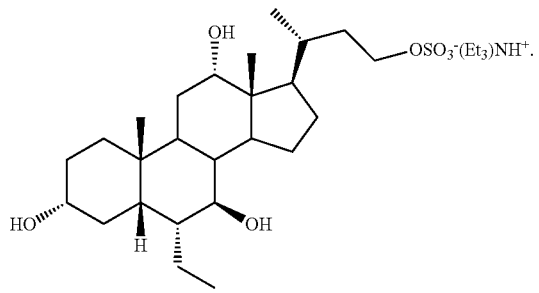

Step B

In one aspect, the present invention relates to a process for preparing a compound of formula I:

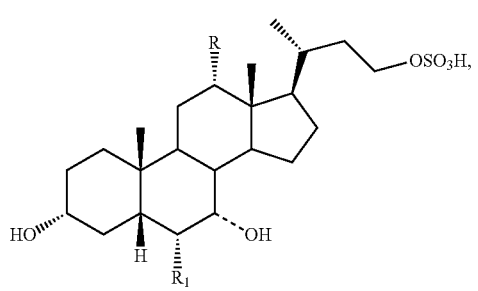

(I)

or a pharmaceutically acceptable salt (e.g., any one of formulae IA, IB, IC, ID, IAA, IBB, ICC, and IDD) or solvate thereof, wherein the dashed bond (----) at position 7 indicates that the substituent is in an α or β stereochemistry;

R is hydrogen or hydroxy; and $R_1$ is hydrogen or $C_1$-$C_6$ alkyl, comprising the step of Step B: converting a compound of formula 3A to a compound of formula 4A:

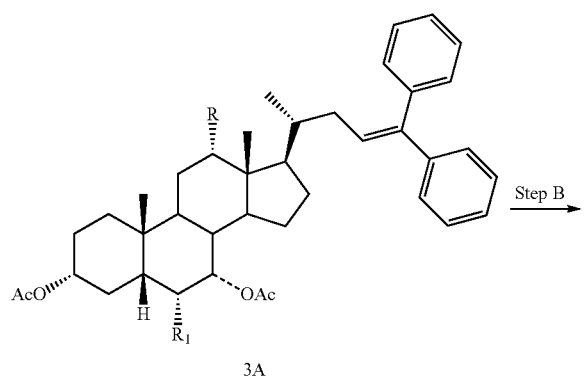

14

-continued

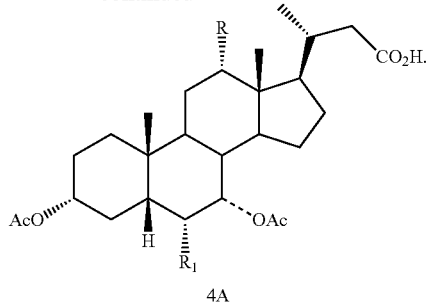

4A

In one aspect, the present invention relates to a process for preparing a compound or a pharmaceutically acceptable salt of formula I, IA, IB, IC, ID, IAA, IBB, ICC, or IDD, wherein in Step B, a compound of formula 3A is reacted with $RuCl_3$, $NaIO_4$, and an acid to form a compound of formula 4A.

In one aspect, the present invention relates to a process for preparing a compound or a pharmaceutically acceptable salt of formula I, IA, IB, IC, ID, IAA, IBB, ICC, or IDD, wherein in Step B, the molar ratio of a compound of formula 3A to $RuCl_3$ is from about 18:1 to about 22:1. In another aspect, the molar ratio is from about 19:1 to about 21:1. In another aspect, the molar ratio is about 20:1.

In one aspect, the present invention relates to a process for preparing a compound or a pharmaceutically acceptable salt of formula I, IA, IB, IC, ID, IAA, IBB, ICC, or IDD, wherein in Step B, the acid is $H_2SO_4$, HCl, $HClO_4$, or $HIO_4$. In another aspect, the acid is 2N $H_2SO_4$. In another aspect, the acid is 2N HCl.

In one aspect, the present invention relates to a process for preparing a compound or a pharmaceutically acceptable salt of formula I, IA, IB, IC, ID, IAA, IBB, ICC, or IDD, wherein in Step B, the molar ratio of a compound of formula 3A to the acid is from about 1:1 to about 4:1. In another aspect, the molar ratio is from about 1:1 to about 3:1. In another aspect, the molar ratio is about 2:1.

In one aspect, the present invention relates to a process for preparing a compound or a pharmaceutically acceptable salt of formula I, IA, IB, IC, ID, IAA, IBB, ICC, or IDD, wherein in Step B, the reaction is carried out in a mixture of solvents. In one aspect, the mixture of solvents comprises one polar protic and two polar aprotic solvents. In one aspect, the polar protic solvent is $H_2O$. In one aspect, the polar aprotic solvents are acetonitrile and ethyl acetate. In one aspect, the polar aprotic solvents are acetonitrile and chloroform. In one aspect, the mixture of solvents is $H_2O$/ethyl acetate/acetonitrile or $H_2O$/chloroform/acetonitrile.

In one aspect, the ratio of $H_2O$ to ethyl acetate to acetonitrile is from about 1:1:1 to about 1:3:2 by volume. In another aspect, the ratio is about 1:1.5:1 to about 1:2.5:1.5 by volume. In one aspect, the ratio is about 1:2:1.5 by volume.

In one aspect, the mixture of solvents comprises one polar protic and one polar aprotic solvents. In one aspect, the polar protic solvent is $H_2O$. In one aspect, the polar aprotic solvent is chloroform, acetonitrile, or acetone. In one aspect, the mixture of solvents is $H_2O$/chloroform, $H_2O$/acetonitrile, or $H_2O$/acetone.

In one aspect, the mixture of solvents comprises two polar protic solvents. In one aspect, the polar protic solvents are $H_2O$ and t-butanol.

In one aspect, the present invention relates to a process for preparing a compound or a pharmaceutically acceptable salt of formula I, IA, IB, IC, ID, IAA, IBB, ICC, or IDD, wherein in Step B, the reaction is carried out at a temperature from about −10° C. to about 10° C. In one aspect, the temperature is from about −5° C. to about 5° C. In one aspect, the temperature is about 0° C.

Step BX

In one aspect, Step BX replaces Step B in Scheme 1. In one aspect, the present invention relates to a process for preparing a compound of formula I:

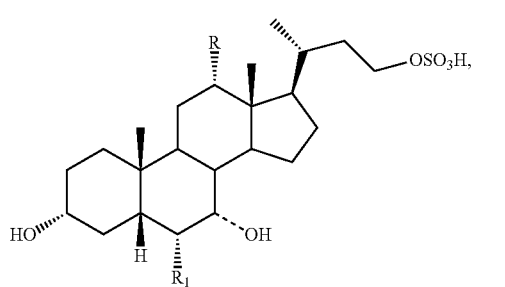

or a pharmaceutically acceptable salt (e.g., any one of formulae IA, IB, IC, ID, IAA, IBB, ICC, and IDD) or solvate thereof, wherein the dashed bond (----) at position 7 indicates that the substituent is in an α or β stereochemistry;

R is hydrogen or hydroxy; and $R_1$ is hydrogen or $C_1$-$C_6$ alkyl, comprising the step of Step BX: converting a compound of formula 3A to a compound of formula 4A:

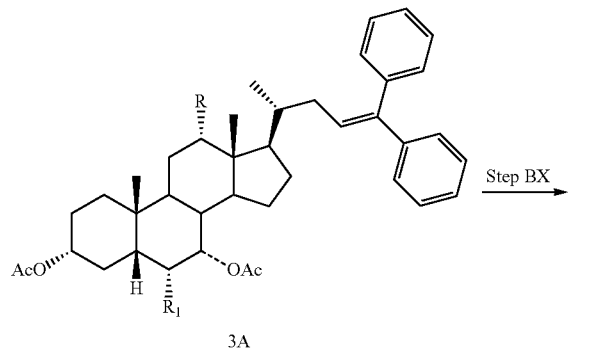

wherein in Step BX, a compound of formula 3A is reacted with $O_3$ gas to form a compound of formula 4A. In one aspect, the $O_3$ gas also contains $O_2$ gas.

In one aspect, the present invention relates to a process for preparing a compound or a pharmaceutically acceptable salt of formula I, IA, IB, IC, ID, IAA, IBB, ICC, or IDD, wherein in Step BX, the gas is bubbled through the reaction mixture at about 4 psi to about 15 psi. In another embodiment, the gas is bubbled through the reaction mixture at about 10 psi to about 15 psi. In another embodiment, the gas is bubbled through the reaction mixture at about 12 psi.

In one aspect, the present invention relates to a process for preparing a compound or a pharmaceutically acceptable salt of formula I, IA, IB, IC, ID, IAA, IBB, ICC, or IDD, wherein in Step BX, the reaction is carried out in a polar aprotic solvent. In one aspect, the polar aprotic solvent is dichloromethane.

In one aspect, the present invention relates to a process for preparing a compound or a pharmaceutically acceptable salt of formula I, IA, IB, IC, ID, IAA, IBB, ICC, or IDD, wherein in Step BX, the reaction is carried out at a temperature from about −73° C. to about −78° C.

Step D

In one aspect, the present invention relates to a process for preparing a compound or a pharmaceutically acceptable salt of formula I, IA, IB, IC, ID, IAA, IBB, ICC, or IDD; comprising the steps of Step B: converting a compound of formula 3A to a compound of formula 4A:

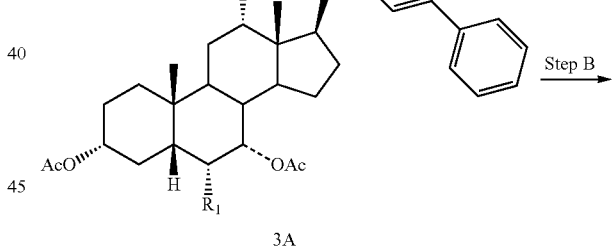

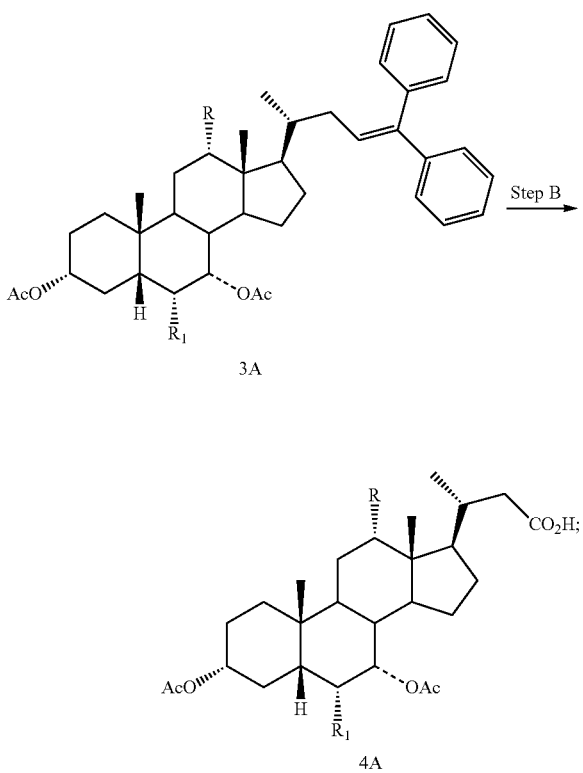

and

Step D: converting a compound of formula 5A to a compound of formula I-Na:

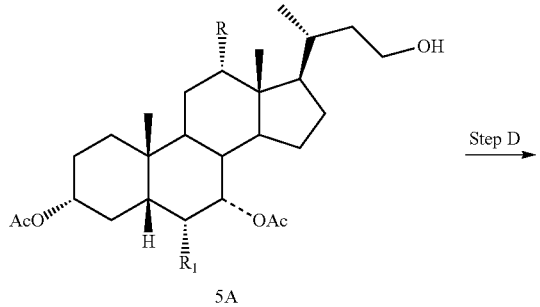

5A

Step D

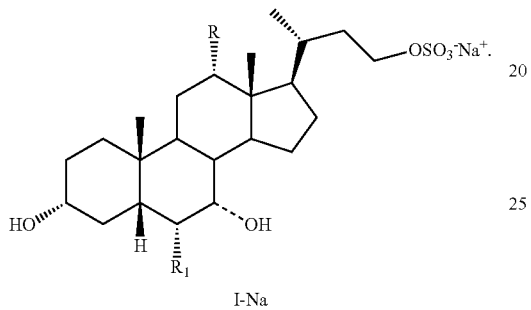

I-Na

In one aspect, the present invention relates to a process for preparing a compound or a pharmaceutically acceptable salt of formula I, IA, IB, IC, ID, IAA, IBB, ICC, or IDD, wherein in Step D, a compound of formula 5A is reacted with a sulfonating agent to form a salt of formula I-Na. In one aspect, the sulfonating agent is sulfur trioxide, chlorosulfonic acid, or sulphamic acid. In another aspect, the sulfonating agent is a sulfur trioxide complex. In another aspect, the sulfur trioxide complex is selected from sulfur trioxide pyridine, sulfur trioxide dioxane, and sulfur trioxide trimethylamine. In another aspect, the sulfur trioxide complex is sulfur trioxide pyridine.

In one aspect, the molar ratio of the sulfonating agent to a compound of formula 5A is from about 4:1 to about 1:1. In another aspect, the molar ratio is from about 3:1 to about 1.5:1. In another aspect, the molar ratio is about 2:1.

In one aspect, the present invention relates to a process for preparing a compound or a pharmaceutically acceptable salt of formula I, IA, IB, IC, ID, IAA, IBB, ICC, or IDD, wherein in Step D, the reaction is carried out in a polar aprotic solvent. In another aspect, the polar aprotic solvent is pyridine.

In one aspect, the present invention relates to a process for preparing a compound or a pharmaceutically acceptable salt of formula I, IA, IB, IC, ID, IAA, IBB, ICC, or IDD, wherein in Step D, the reaction is carried out at a temperature from about 10° C. to about 30° C. In one aspect, the temperature is from about 15° C. to about 25° C. In another aspect, the temperature is from about 20° C. to about 23° C.

In one aspect, the present invention relates to a process for preparing a compound or a pharmaceutically acceptable salt of formula I, IA, IB, IC, ID, IAA, IBB, ICC, or IDD, wherein in Step D, the reaction mixture is under inert atmosphere. In another aspect, the inert atmosphere is a nitrogen atmosphere.

In one aspect, the present invention relates to a process for preparing a compound or a pharmaceutically acceptable salt of formula I, IA, IB, IC, ID, IAA, IBB, ICC, or IDD, wherein in Step D, during workup, the residue from the reaction mixture is treated with a base and a polar protic solvent. In one aspect, the polar protic solvent is a $C_1$-$C_6$ alcohol. In one aspect, polar protic solvent is $C_1$-$C_3$ alcohol. In one aspect, the polar protic solvent is $CH_3OH$. In one aspect, the base is NaOH. In one aspect, the base is 10% (w/w) solution of NaOH in $CH_3OH$.

Step C

In one aspect, the present invention relates to a process for preparing a compound or a pharmaceutically acceptable salt of formula I, IA, IB, IC, ID, IAA, IBB, ICC, or IDD, comprising the steps of Step B: converting a compound of formula 3A to a compound of formula 4A:

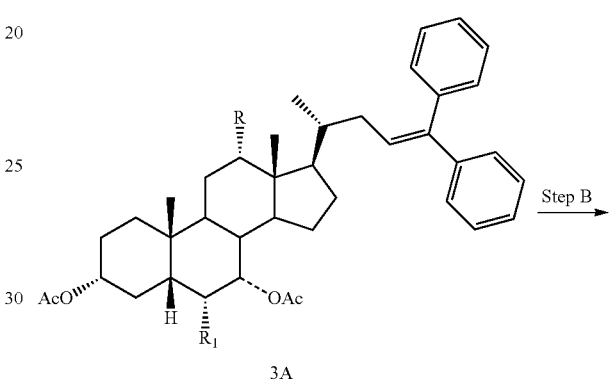

3A

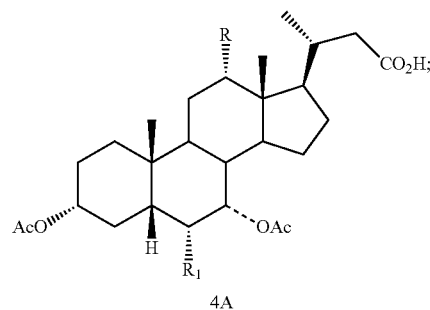

4A

Step C: converting a compound of formula 4A to a compound of formula 5A:

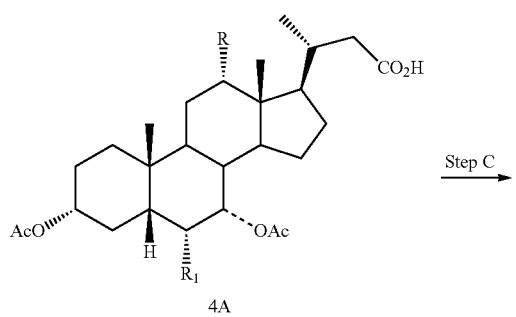

4A

-continued

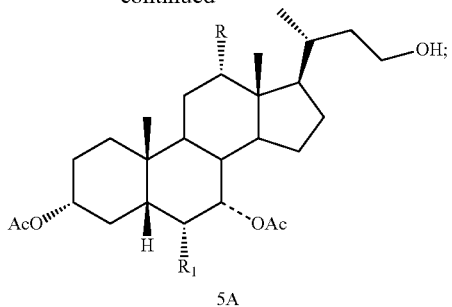

5A and

Step D: converting a compound of formula 5A to a compound of formula I-Na:

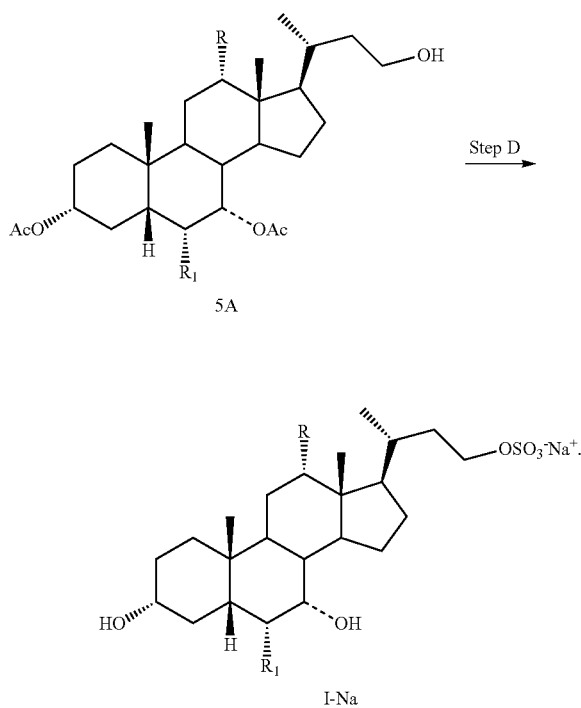

In one aspect, the present invention relates to a process for preparing a compound or a pharmaceutically acceptable salt of formula I, IA, IB, IC, ID, IAA, IBB, ICC, or IDD, wherein in Step C, a compound of formula 4A is reacted with a reducing agent to form a compound of formula 5A.

In one aspect, the present invention relates to a process for preparing a compound or a pharmaceutically acceptable salt of formula I, IA, IB, IC, ID, IAA, IBB, ICC, or IDD, further comprising in Step C, reacting a compound of formula 4A with a reagent to form an anhydride of a compound of formula 4A.

In one aspect, the present invention relates to a process for preparing a compound or a pharmaceutically acceptable salt of formula I, IA, IB, IC, ID, IAA, IBB, ICC, or IDD, further comprising in Step C, reacting a compound of formula 4A with a chloroformate reagent and a base to form an anhydride of a compound of formula 4A.

In one aspect, the present invention relates to a process for preparing a compound or a pharmaceutically acceptable salt of formula I, IA, IB, IC, ID, IAA, IBB, ICC, or IDD, further comprising in Step C, reacting an anhydride of a compound of formula 4A with a reagent to form a compound of formula 5A.

In one aspect, the present invention relates to a process for preparing a compound or a pharmaceutically acceptable salt of formula I, IA, IB, IC, ID, IAA, IBB, ICC, or IDD, further comprising in Step C, reacting an anhydride of a compound of formula 4A with a hydride to form a compound of formula 5A.

In one aspect, the present invention relates to a process for preparing a compound or a pharmaceutically acceptable salt of formula I, IA, IB, IC, ID, IAA, IBB, ICC, or IDD, wherein in Step C, the hydride is $NaBH_4$, Na/t-BuOH, $LiAlH_4$, $NaAlH_2(OC_2H_4OCH_3)_2$, or $LiBH_4$. In another aspect, the hydride is $NaBH_4$.

In one aspect, the molar ratio of $NaBH_4$ to a compound of formula 4A is from about 50:1 to about 60:1. In another aspect, the molar ratio is from about 54:1 to about 57:1. In another aspect, the molar ratio is about 56:1.

In one aspect, the present invention relates to a process for preparing a compound or a pharmaceutically acceptable salt of formula I, IA, IB, IC, ID, IAA, IBB, ICC, or IDD, wherein in Step C, the chloroformate reagent is isobutyl chloroformate, ethyl chloroformate, isopropyl chloroformate, or t-butyl chloroformate. In one aspect, the chloroformate reagent is isobutyl chloroformate.

In one aspect, the molar ratio of isobutyl chloroformate to a compound of formula 4A is from about 1:1 to about 1.5:1. In another aspect, molar ratio is from about 1.1:1 to about 1.3:1. In one aspect, the molar ratio is about 1.2:1.

In one aspect, the present invention relates to a process for preparing a compound or a pharmaceutically acceptable salt of formula I, IA, IB, IC, ID, IAA, IBB, ICC, or IDD, wherein in Step C, the base is triethylamine. In one aspect, the molar ratio of triethylamine to a compound of formula 4A is from about 1:1 to about 2:1. In another aspect, the molar ratio is from about 1.1:1 to about 1.7:1. In another aspect, the molar ratio is about 1.3:1.

In one aspect, the present invention relates to a process for preparing a compound or a pharmaceutically acceptable salt of formula I, IA, IB, IC, ID, IAA, IBB, ICC, or IDD, wherein in Step C, the reaction is carried out in a polar aprotic solvent. In one aspect, the polar aprotic solvent is tetrahydrofuran.

In one aspect, the present invention relates to a process for preparing a compound or a pharmaceutically acceptable salt of formula I, IA, IB, IC, ID, IAA, IBB, ICC, or IDD, wherein in Step C, the reaction is carried out at a temperature from about −10° C. to about 10° C. In one aspect, the temperature is from about −5° C. to about 5° C. In another aspect, the temperature is about 0° C.

In one aspect, the present invention relates to a process for preparing a compound or a pharmaceutically acceptable salt of formula I, IA, IB, IC, ID, IAA, IBB, ICC, or IDD, wherein in Step C during workup, the reaction mixture is quenched with $H_2O$ and then acidified with an acid. In one aspect, the acid is HCl.

The Process of Scheme 2

In one aspect, the present invention relates to a process for preparing a compound of formula I:

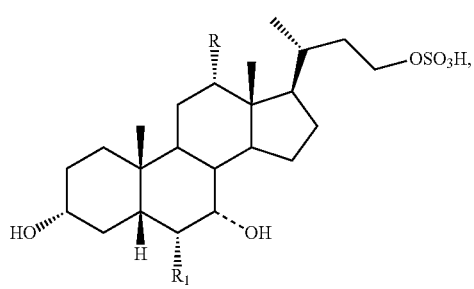

or a pharmaceutically acceptable salt or solvate thereof, wherein the dashed bond (----) at position 7 indicates that the substituent is in an α or β stereochemistry;

R is hydrogen or hydroxy; and $R_1$ is hydrogen or $C_1$-$C_6$ alkyl, comprising the steps of Step 1: converting a compound of formula II to a compound of formula III:

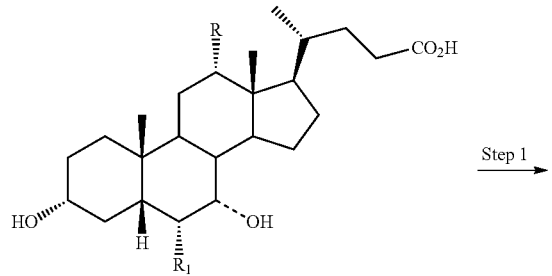

Step 2: converting a compound of formula III to a compound of formula IV:

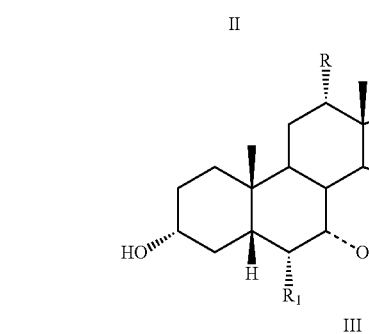

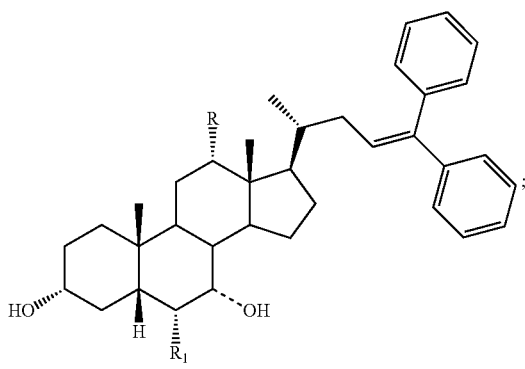

Step 3: converting a compound of formula IV to a compound of formula V:

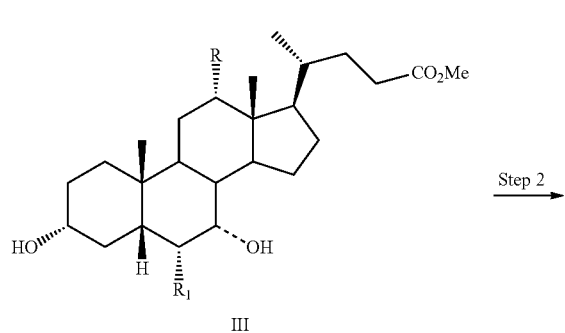

Step 4: converting a compound of formula V to a compound of formula VI:

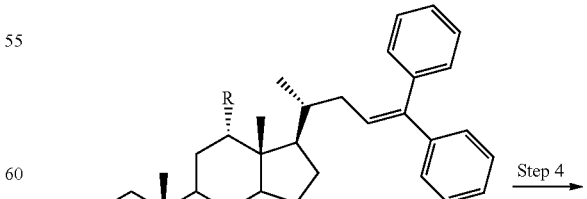

-continued

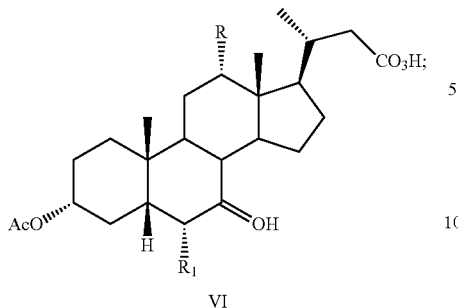

VI

Step 5: converting a compound of formula VI to a compound of formula VII:

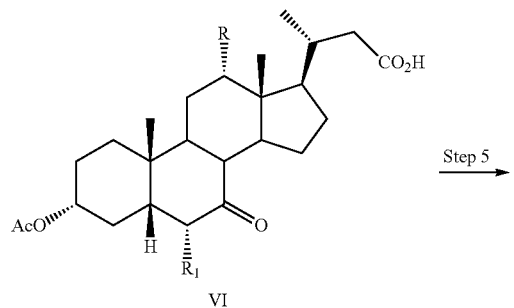

VI and

Step 6: converting a compound of formula VII to a compound of formula I-Na:

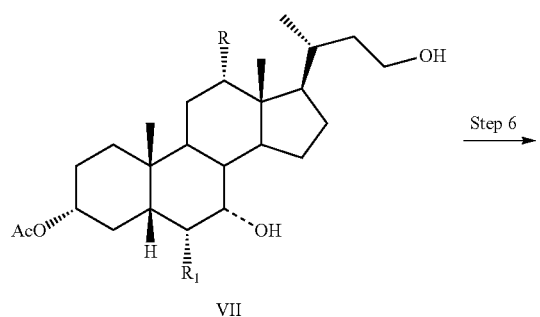

VII

-continued

I-Na

In one aspect, the present invention relates to a process for preparing a compound or a pharmaceutically acceptable salt of formula I, wherein R is hydroxy. In another aspect, R is hydrogen. In one aspect, $R_1$ is $C_1$-$C_6$ alkyl. In one aspect, $R_1$ is methyl. In another aspect, $R_1$ is ethyl. In another aspect, $R_1$ is propyl. In another aspect, R is hydrogen and $R_1$ is $C_1$-$C_6$ alkyl. In another aspect, R is hydroxyl and $R_1$ is $C_1$-$C_6$ alkyl. In another aspect, R is hydrogen and $R_1$ is $C_1$-$C_3$ alkyl. In another aspect, R is hydroxyl and $R_1$ is $C_1$-$C_3$ alkyl.

In one aspect, the present invention relates to a process for preparing a compound of formula I, or a pharmaceutically acceptable salt or solvate thereof, wherein the salt is selected from (IA)

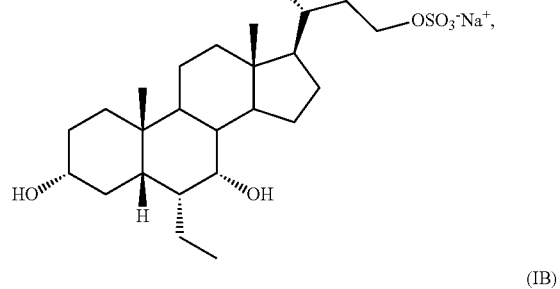

(IB)

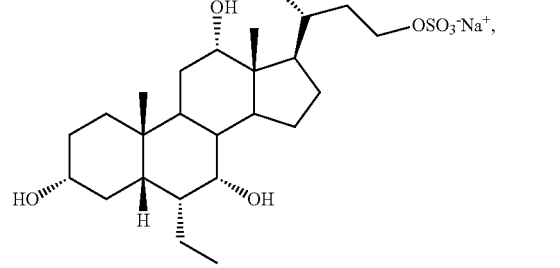

(IC)

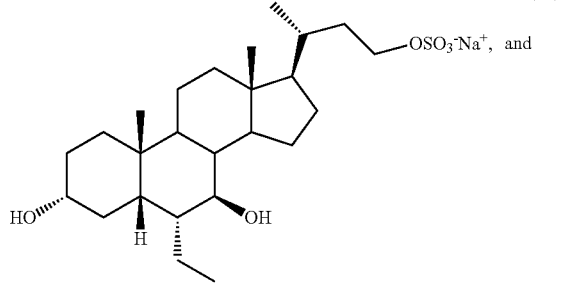

25
-continued (ID)
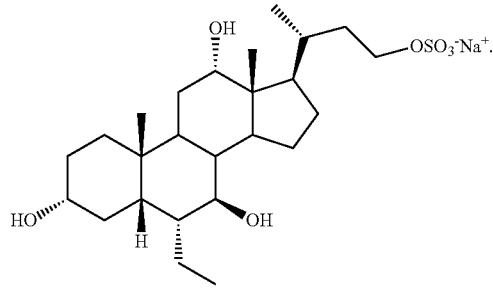

In one aspect, the present invention relates to a process for preparing a compound of formula I, or a pharmaceutically acceptable salt or solvate thereof, wherein the salt is selected from (IAA)
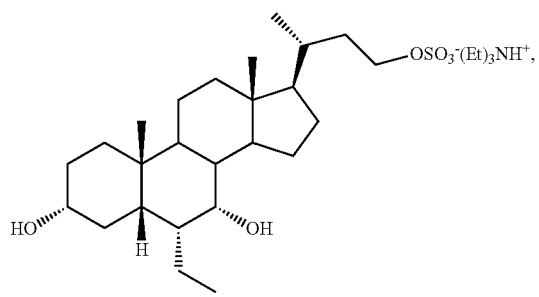

(IBB)
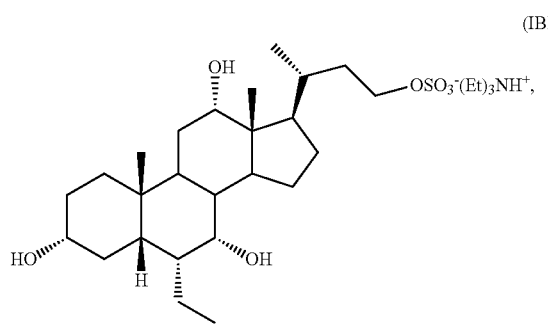

(ICC)
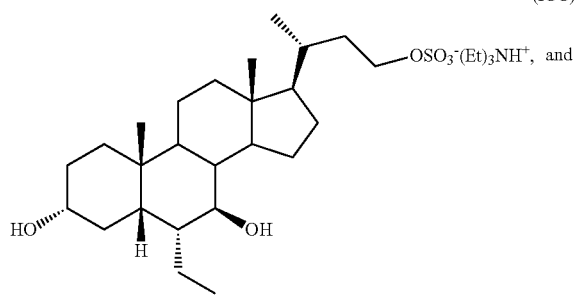

26
-continued (IDD)
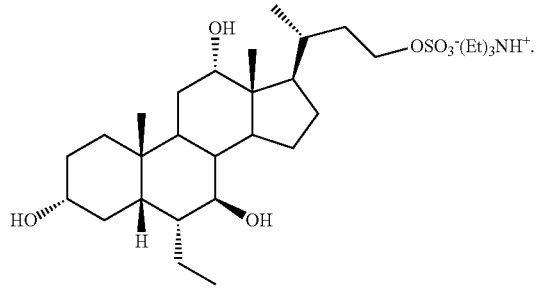

Step 4

In one aspect, the present invention relates a process for preparing a compound of formula I:

(I)
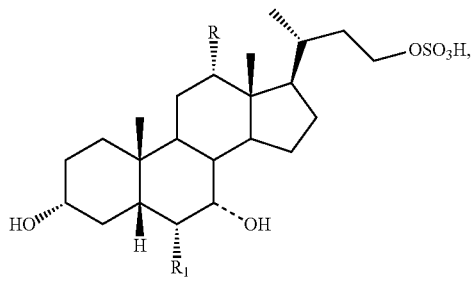

or a pharmaceutically acceptable salt (e.g., any one of formulae IA, IB, IC, ID, IAA, IBB, ICC, and IDD) or solvate thereof, wherein the dashed bond (----) at position 7 indicates that the substituent is in an α or β stereochemistry;

R is hydrogen or hydroxy; and $R_1$ is hydrogen or $C_1$-$C_6$ alkyl, comprising the step of Step 4: converting a compound of formula V to a compound of formula VI:

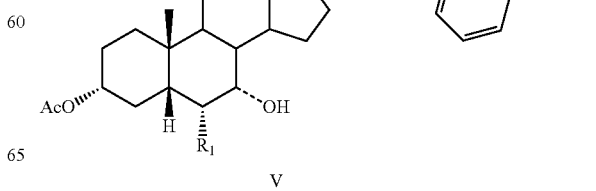

V

-continued

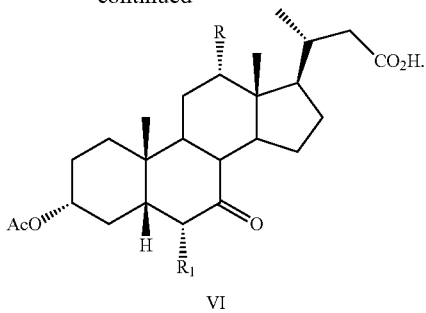

VI

In one aspect, the present invention relates to a process for preparing a compound or a pharmaceutically acceptable salt of formula I, IA, IB, IC, ID, IAA, IBB, ICC, or IDD, wherein in Step 4, a compound of formula V is reacted with $RuCl_3$, $NaIO_4$, and an acid to form a compound of formula VI.

In one aspect, the present invention relates to a process for preparing a compound or a pharmaceutically acceptable salt of formula I, IA, IB, IC, ID, IAA, IBB, ICC, or IDD, wherein in Step 4, the molar ratio of a compound of formula V to $RuCl_3$ is from about 18:1 to about 22:1. In one aspect, the molar ratio is from about 19:1 to about 21:1. In another aspect, the molar ratio is about 20:1.

In one aspect, the present invention relates to a process for preparing a compound or a pharmaceutically acceptable salt of formula I, IA, IB, IC, ID, IAA, IBB, ICC, or IDD, wherein in Step 4, the acid is $H_2SO_4$, HCl, $HClO_4$, or $HIO_4$. In one aspect, the acid is 2N $H_2SO_4$. In another aspect, the acid is 2N HCl.

In one aspect, the present invention relates to a process for preparing a compound or a pharmaceutically acceptable salt of formula I, IA, IB, IC, ID, IAA, IBB, ICC, or IDD, wherein in Step 4, the molar ratio of a compound of formula V to the acid is from about 2:1 to about 6:1. In one aspect, the molar ratio is from about 5:1 to about 3:1. In another aspect, the molar ratio is about 4:1.

In one aspect, the present invention relates to a process for preparing a compound or a pharmaceutically acceptable salt of formula I, IA, IB, IC, ID, IAA, IBB, ICC, or IDD, wherein in Step 4, the reaction is carried out in a mixture of solvents. In one aspect, the mixture of solvents comprises one polar protic and two polar aprotic solvents. In one aspect, the polar protic solvent is $H_2O$. In one aspect, the polar aprotic solvents are acetonitrile and ethyl acetate.

In one aspect, the polar aprotic solvents are acetonitrile and chloroform. In one aspect, the mixture of solvents is $H_2O$/ethyl acetate/acetonitrile or $H_2O$/chloroform/acetonitrile.

In one aspect, the ratio of $H_2O$ to ethyl acetate to acetonitrile is from about 1:1:1 to about 1:3:2 by volume. In another aspect, the ratio is about 1:1.5:1 to about 1:2.5:1.5 by volume. In another aspect, the ratio is about 1:2:1.5 by volume.

In one aspect, the mixture of solvents comprises one polar protic and one polar aprotic solvents. In another aspect, the polar protic solvent is $H_2O$. In one aspect, the polar aprotic solvent is chloroform, acetonitrile, or acetone. In one aspect, the mixture of solvents is $H_2O$/chloroform, $H_2O$/acetonitrile, or $H_2O$/acetone.

In one aspect, the mixture of solvents comprises two polar protic solvents. In one aspect, polar protic solvents are $H_2O$ and t-butanol.

In one aspect, the present invention relates to a process for preparing a compound or a pharmaceutically acceptable salt of formula I, IA, IB, IC, ID, IAA, IBB, ICC, or IDD, wherein in Step 4, the reaction is carried out at a temperature from about −10° C. to about 10° C. In another aspect, the temperature is from about −5° C. to about 5° C. In another aspect, the temperature is about 0° C.

Step 4X

In one aspect of the invention, Step 4X replaces Step 4 in Scheme 2. In one aspect, the present invention relates to a process for preparing a compound of formula I:

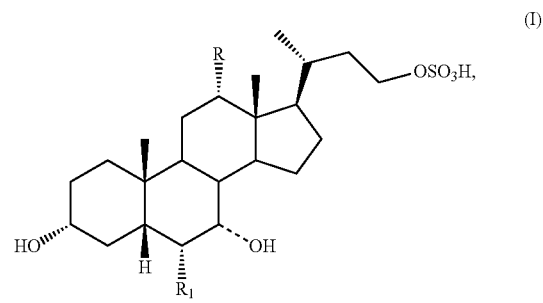

(I)

or a pharmaceutically acceptable salt (e.g., any one of formulae IA, IB, IC, ID, IAA, IBB, ICC, and IDD) or solvate thereof, wherein the dashed bond (----) at position 7 indicates that the substituent is in an α or β stereochemistry;

R is hydrogen or hydroxy; and $R_1$ is hydrogen or $C_1$-$C_6$ alkyl, comprising the step of Step 4X: converting a compound of formula V to a compound of formula VII:

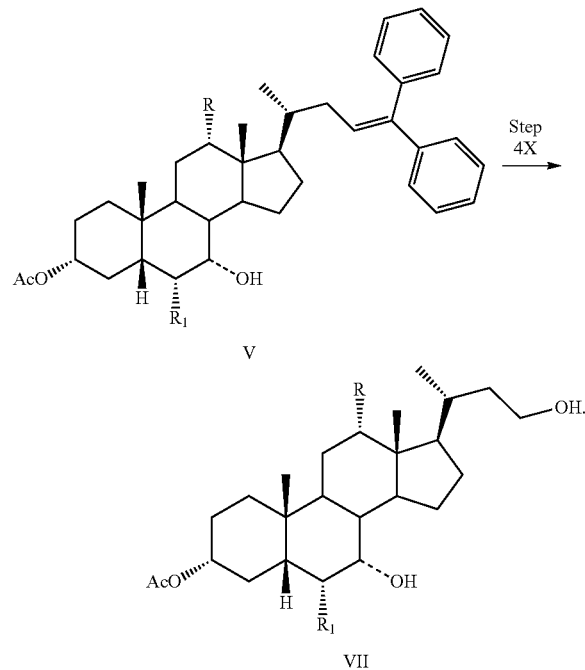

In one aspect, the present invention relates to a process for preparing a compound or a pharmaceutically acceptable salt of formula I, IA, IB, IC, ID, IAA, IBB, ICC, or IDD, wherein in Step 4X, a compound of formula V is reacted with O₃ gas to form a compound of formula VII. In one aspect, the O₃ gas also contains O₂ gas.

In one aspect, the present invention relates to a process for preparing a compound or a pharmaceutically acceptable salt of formula I, IA, IB, IC, ID, IAA, IBB, ICC, or IDD, wherein in Step 4X, the gas is bubbled through the reaction mixture at about 4 psi to about 15 psi. In one aspect, the gas is bubbled through the reaction mixture at about 10 psi to about 15 psi. In another aspect, the gas is bubbled through the reaction mixture at about 12 psi.

In one aspect, the present invention relates to a process for preparing a compound or a pharmaceutically acceptable salt of formula I, IA, IB, IC, ID, IAA, IBB, ICC, or IDD, wherein in Step 4X, the reaction is carried out in a polar aprotic solvent. In one aspect, the polar aprotic solvent is dichloromethane.

In one aspect, the present invention relates to a process for preparing a compound or a pharmaceutically acceptable salt of formula I, IA, IB, IC, ID, IAA, IBB, ICC, or IDD, wherein in Step 4X, the reaction is carried out at a temperature from about −73° C. to about −78° C.

In one aspect, the present invention relates to a process for preparing a compound or a pharmaceutically acceptable salt of formula I, IA, IB, IC, ID, IAA, IBB, ICC, or IDD, further comprising in Step 4X, reacting a compound of formula V with NaBH₄ in an inert atmosphere.

In one aspect, the present invention relates to a process for preparing a compound or a pharmaceutically acceptable salt of formula I, IA, IB, IC, ID, IAA, IBB, ICC, or IDD, wherein the molar ratio of a compound of formula V to NaBH₄ is from about 1:2 to about 1:4. In one aspect, the molar ratio of a compound of formula V to NaBH₄ is about 1:3.

In one aspect, the present invention relates to a process for preparing a compound or a pharmaceutically acceptable salt of formula I, IA, IB, IC, ID, IAA, IBB, ICC, or IDD, further comprising in Step 4X, adding to the reaction mixture a polar protic solvent. In one aspect, the polar aprotic solvent is selected from methanol and ethanol.

In one aspect, the present invention relates to a process for preparing a compound or a pharmaceutically acceptable salt of formula I, IA, IB, IC, ID, IAA, IBB, ICC, or IDD, wherein the inert atmosphere is a nitrogen atmosphere.

In one aspect, the present invention relates to a process for preparing a compound or a pharmaceutically acceptable salt of formula I, IA, IB, IC, ID, IAA, IBB, ICC, or IDD, wherein in Step 4X, during workup, an acid is added to the reaction mixture. In one aspect, the acid is HCl.

Step 6

In one aspect, the present invention relates to a process for preparing a compound or a pharmaceutically acceptable salt of formula I, IA, IB, IC, ID, IAA, IBB, ICC, or IDD; comprising the steps of Step 4: converting a compound of formula V to a compound of formula VI:

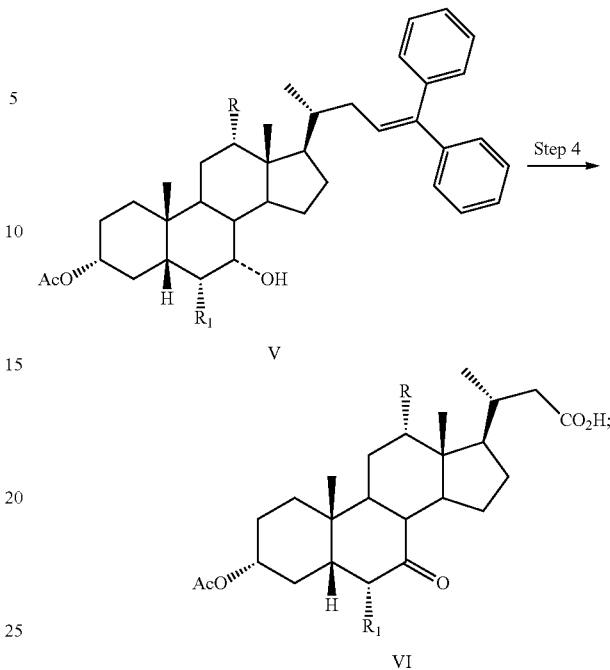

and

Step 6: converting a compound of formula VII to a salt of formula I-Na:

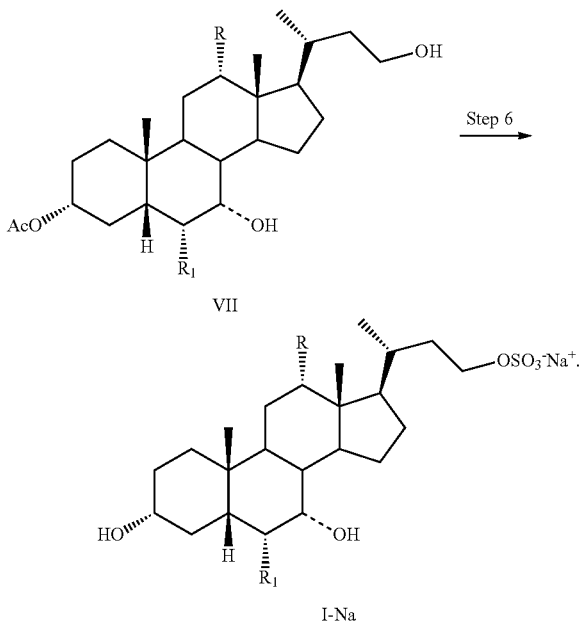

In one aspect, the present invention relates to a process for preparing a compound or a pharmaceutically acceptable salt of formula I, IA, IB, IC, ID, IAA, IBB, ICC, or IDD, wherein in Step 6, a compound of formula VII is reacted with a sulfonating agent to form a salt of formula I-Na. In one aspect, the sulfonating agent is sulfur trioxide, chlorosulfonic acid, or sulphamic acid. In one aspect, the sulfonating agent is a sulfur trioxide complex. In one aspect, the sulfur trioxide complex is selected from sulfur trioxide pyridine, sulfur trioxide dioxane, and sulfur trioxide trimethylamine. In one aspect, the sulfur trioxide complex is sulfur trioxide pyridine.

In one aspect, the molar ratio of the sulfonating agent to a compound of formula VII is from about 2:1 to about 1:1. In another aspect, the molar ratio is from about 1.5:1 to about 1.2:1. In another aspect, the molar ratio is about 1.4:1. In another aspect, the molar ratio is about 1.35:1.

In one aspect, the present invention relates to a process for preparing a compound or a pharmaceutically acceptable salt of formula I, IA, IB, IC, ID, IAA, IBB, ICC, or IDD, wherein in Step 6, the reaction is carried out in a polar aprotic solvent. In one aspect, the polar aprotic solvent is pyridine.

In one aspect, the present invention relates to a process for preparing a compound or a pharmaceutically acceptable salt of formula I, IA, IB, IC, ID, IAA, IBB, ICC, or IDD, wherein in Step 6, the reaction is carried out at a temperature from about 10° C. to about 30° C. In another aspect, the temperature is from about 15° C. to about 25° C. In another aspect, the temperature is from about 20° C. to about 23° C.

In one aspect, the present invention relates to a process for preparing a compound or a pharmaceutically acceptable salt of formula I, IA, IB, IC, ID, IAA, IBB, ICC, or IDD, wherein in Step 6, the reaction is under inert atmosphere. In another aspect, the inert atmosphere is a nitrogen atmosphere.

In one aspect, the present invention relates to a process for preparing a compound or a pharmaceutically acceptable salt of formula I, IA, IB, IC, ID, IAA, IBB, ICC, or IDD, wherein in Step 6, during workup, the residue from the reaction mixture is treated with a base and a polar protic solvent. In one aspect, the polar protic solvent is a $C_1$-$C_6$ alcohol. In one aspect, the polar protic solvent is $C_1$-$C_3$ alcohol. In one aspect, the polar protic solvent is $CH_3OH$. In one aspect, the base is NaOH. In one aspect, the base is 10% (w/w) solution of NaOH in $CH_3OH$.

Step 5

In one aspect, the present invention relates to a process for preparing a compound or a pharmaceutically acceptable salt of formula I, IA, IB, IC, ID, IAA, IBB, ICC, or IDD, comprising the steps of Step 4: converting a compound of formula V to a compound of formula VI:

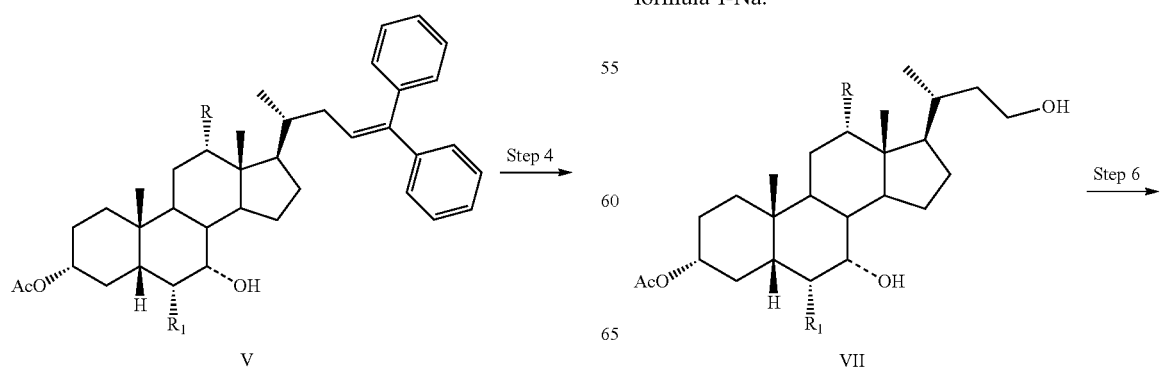

V

Step 5: converting a compound of formula VI to a compound of formula VII:

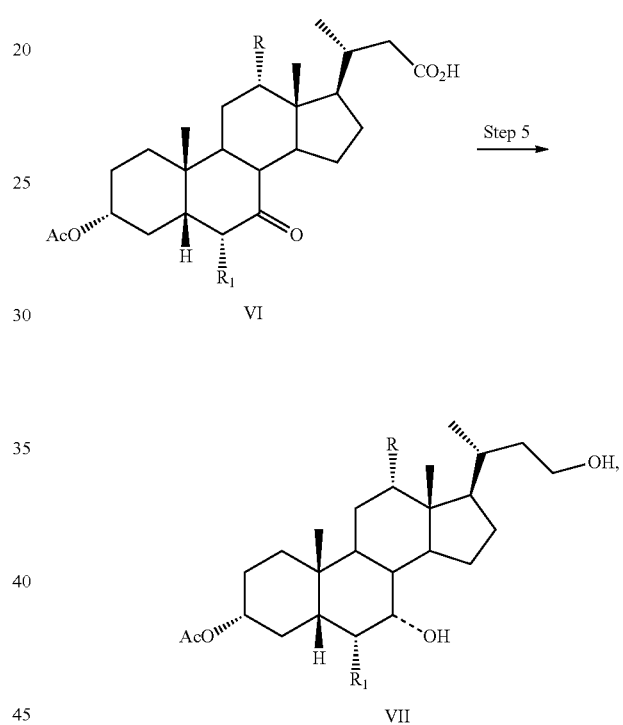

and

Step 6: converting a compound of formula VII to a salt of formula I-Na:

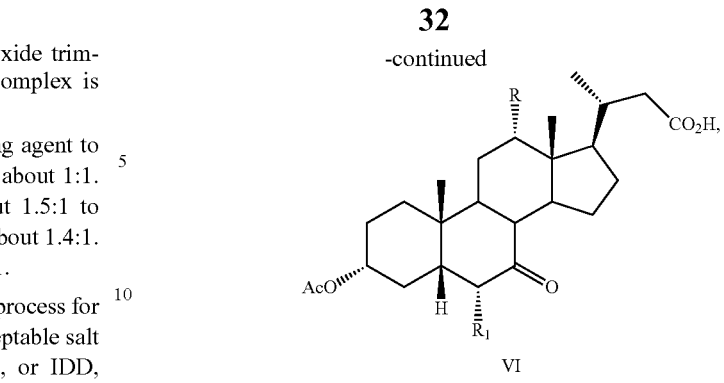

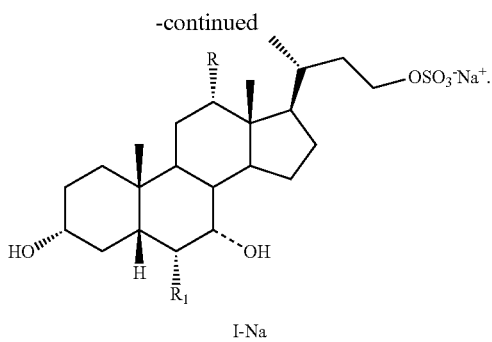

I-Na

In one aspect, the present invention relates to a process for preparing a compound or a pharmaceutically acceptable salt of formula I, IA, IB, IC, ID, IAA, IBB, ICC, or IDD, wherein in Step 5, a compound of formula VI is reacted with a reducing agent to form a compound of formula VII.

In one aspect, the present invention relates to a process for preparing a compound or a pharmaceutically acceptable salt of formula I, IA, IB, IC, ID, IAA, IBB, ICC, or IDD, further comprising in Step 5, reacting a compound of formula VI with a reagent to form an anhydride of a compound of formula VI.

In one aspect, the present invention relates to a process for preparing a compound or a pharmaceutically acceptable salt of formula I, IA, IB, IC, ID, IAA, IBB, ICC, or IDD, further comprising in Step 5, reacting a compound of formula VI with a chloroformate reagent and a base to form an anhydride of a compound of formula VI.

In one aspect, the present invention relates to a process for preparing a compound or a pharmaceutically acceptable salt of formula I, IA, IB, IC, ID, IAA, IBB, ICC, or IDD, further comprising in Step 5, reacting an anhydride of a compound of formula VI with a reagent to form a compound of formula VII.

In one aspect, the present invention relates to a process for preparing a compound or a pharmaceutically acceptable salt of formula I, IA, IB, IC, ID, IAA, IBB, ICC, or IDD, further comprising in Step 5, reacting an anhydride of a compound of formula VI with a hydride to form a compound of formula VII.

In one aspect, the hydroxy group at position 7 of the compound of formula VII is in the α position. In another aspect, the hydroxy group at position 7 of the compound of formula VII is in the β position.

In one aspect, the hydride is $NaBH_4$, Na/t-BuOH, $LiAlH_4$, $NaAlH_2(OC_2H_4OCH_3)_2$, or $LiBH_4$. In another aspect, the hydride is $NaBH_4$. In one aspect, the molar ratio of $NaBH_4$ to a compound of formula VI is from about 8:1 to about 12:1. In another aspect, the molar ratio is from about 9:1 to about 11:1. In another aspect, the molar ratio is about 10:1.

In one aspect, the present invention relates to a process for preparing a compound or a pharmaceutically acceptable salt of formula I, IA, IB, IC, ID, IAA, IBB, ICC, or IDD, wherein in Step 5, the chloroformate reagent is isobutyl chloroformate, ethyl chloroformate, isopropyl chloroformate, or t-butyl chloroformate. In one aspect, the chloroformate reagent is isobutyl chloroformate.

In one aspect, molar ratio of isobutyl chloroformate to a compound of formula VI is from about 1:1 to about 1.5:1. In one aspect, the molar ratio is from about 1.1:1 to about 1.3:1. In one aspect, the molar ratio is about 1.2:1.

In one aspect, the present invention relates to a process for preparing a compound or a pharmaceutically acceptable salt of formula I, IA, IB, IC, ID, IAA, IBB, ICC, or IDD, wherein in Step 5, the base is triethylamine. In one aspect, molar ratio of triethylamine to a compound of formula VI is from about 1:1 to about 2:1. In another aspect, molar ratio is from about 1.3:1 to about 1.7:1. In another aspect, the molar ratio is about 1.5:1.

In one aspect, the present invention relates to a process for preparing a compound or a pharmaceutically acceptable salt of formula I, IA, IB, IC, ID, IAA, IBB, ICC, or IDD, wherein in Step 5, the reaction is carried out in a polar aprotic solvent. In one aspect, the polar aprotic solvent is tetrahydrofuran.

In one aspect, the present invention relates to a process for preparing a compound or a pharmaceutically acceptable salt of formula I, IA, IB, IC, ID, IAA, IBB, ICC, or IDD, wherein in Step 5, the reaction is carried out at a temperature from about −10° C. to about 10° C. In one aspect, the temperature is from about −5° C. to about 5° C. In another aspect, the temperature is about 0° C.

In one aspect, the present invention relates to a process for preparing a compound or a pharmaceutically acceptable salt of formula I, IA, IB, IC, ID, IAA, IBB, ICC, or IDD, wherein in Step 5 during workup, the reaction mixture is quenched with $H_2O$ and then acidified with an acid. In one aspect, the acid is HCl.

Definitions

For convenience, certain terms used in the specification, examples and appended claims are collected here.

For the avoidance of doubt, the term "a compound of the invention" refers to a compound disclosed herein e.g., a compound of the invention includes compounds of formulae I, IA, IB, IC, ID, IAA, IBB, ICC and IDD. Whenever the term is used in the context of the present invention it is to be understood that the reference is being made to both the free form and the corresponding pharmaceutically acceptable salts and solvates provided that such is possible and/or appropriate under the circumstances.

As used herein, the tem "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "pharmaceutically acceptable salt" of a compound means a salt that is pharmaceutically acceptable and that possesses the desired pharmacological activity of the parent compound.

As used herein, the term "process of the invention" refers to a method for preparing compounds of the invention as described herein, wherein the method comprises any one or more of the steps described in Scheme 1 or Scheme 2.

As used herein, the term "molar ratio" refers to the ratio of equivalents in mole of X to equivalents in mole of Y, where X and Y can be, for example, reagents in a reaction mixture.

When an atom or chemical moiety is followed by a subscripted numeric range (e.g., $C_{1-6}$), the invention is meant to encompass each number within the range as well as all intermediate ranges. For example, "$C_{1-6}$ alkyl" is meant to include alkyl groups with 1, 2, 3, 4, 5, 6, 1-6, 1-5, 1-4, 1-3, 1-2, 2-6, 2-5, 2-4, 2-3, 3-6, 3-5, 3-4, 4-6, 4-5, and 5-6 carbons. As used herein, "alkyl" or "$C_1$, $C_2$, $C_3$, $C_4$, $C_5$, or $C_6$ alkyl" or "$C_{1-6}$ alkyl" is intended to include $C_1$, $C_2$, $C_3$, $C_4$, $C_5$, or $C_6$ straight-chain (linear) saturated aliphatic hydrocarbon groups and $C_3$, $C_4$, $C_5$, or $C_6$ branched saturated aliphatic hydrocarbon groups. For example, $C_{1-6}$ alkyl is intended to include $C_1$, $C_2$, $C_3$, $C_4$, $C_5$, and $C_6$ alkyl groups. Examples of alkyl include, but are not limited to, methyl, ethyl, n-propyl, i-propyl, n-butyl, s-butyl, t-butyl, n-pentyl, s-pentyl, and n-hexyl.

As used herein, the term "Ac" means acetyl.

As used herein, the term "THF" means tetrahydrofuran.

As used herein, the term "DCM" means dichloromethane or methylene chloride.

As used herein, the term "EtOAc" means ethyl acetate.

As used herein, the term "TLC" means thin-layer chromatography.

As used herein, the term "dashed bond (----)" refers two possible positions at the point the substituent to which the dashed bond is connected. For example, when position 7 of formula I is in an α steterochemistry, the structure is as follows:

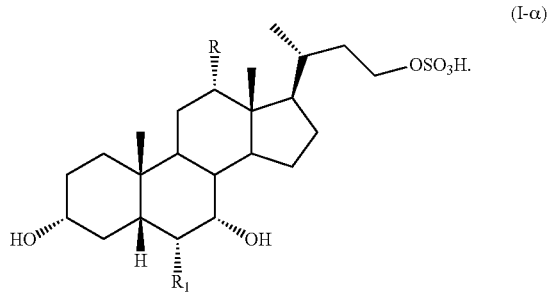

(I-α)

When position 7 of formula I is β, the structure is as follows:

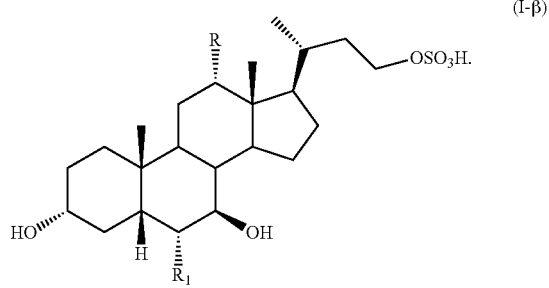

(I-β)

It is to be understood accordingly that the isomers arising from asymmetric carbon atoms (e.g., all enantiomers and diastereomers) are included within the scope of the invention, unless indicated otherwise. Such isomers can be obtained in substantially pure form by classical separation techniques and by stereochemically controlled synthesis. Furthermore, the structures and other compounds and moieties discussed in this application also include all tautomers thereof. Compounds of the invention and synthetic intermediates may exist in stereoisomeric form, therefore can be produced as individual stereoisomers or as mixtures.

As used herein, the term "anhydride of a compound of formula VI" refers to a compound having the structure:

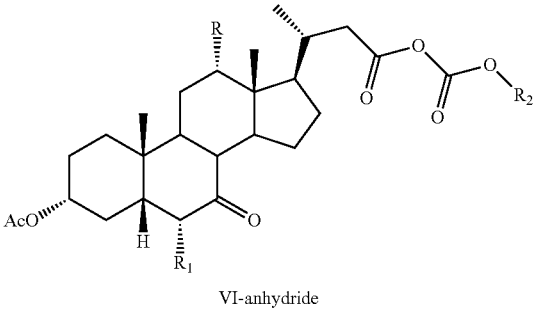

VI-anhydride wherein $R_2$ is $C_1$-$C_6$ alkyl or benzyl.

The invention also comprehends isotopically-labeled compounds of the invention, which are identical to those recited in formulae I, IA, IB, IC, ID, IAA, IBB, ICC and IDD, but for the fact that one or more atoms are replaced by an atom having an atomic mass or mass number different from the atomic mass or mass number most commonly found in nature. Examples of isotopes that can be incorporated into compounds of the invention include isotopes of hydrogen, carbon, nitrogen, fluorine, such as $^3H$, $^{11}C$ and $^{14}C$.

Isotopically labeled compounds of the invention can generally be prepared by carrying out the procedures disclosed in the Schemes and/or in the Examples of the invention, by substituting a readily available isotopically labeled reagent for a non-isotopically labeled reagent. In one aspect, a compound of the invention is not isotopically labelled.

"Solvates" means solvent addition forms that contain either stoichiometric or non stoichiometric amounts of solvent. A compound of the invention may have a tendency to trap a fixed molar ratio of solvent molecules in the crystalline solid state, thus forming a solvate. If the solvent is water, the solvate formed is a hydrate; when the solvent is alcohol, the solvate formed is an alcoholate. Hydrates are formed by the combination of one or more molecules of water with one of the substances in which the water retains its molecular state as $H_2O$, such combination being able to form one or more hydrate. Additionally, the compounds of the invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Tautomers" refers to compounds whose structures differ markedly in arrangement of atoms, but which exist in easy and rapid equilibrium. It is to be understood that the compounds of the invention may be depicted as different tautomers. It should also be understood that when compounds of the invention and synthetic intermediates of the invention have tautomeric forms, all tautomeric forms are intended to be within the scope of the invention, and the naming of the compounds of the invention does not exclude any tautomer form. The compounds of the invention and synthetic intermediates of the invention can exist in several tautomeric forms, including the keto-enol. For example, in keto-enol tautomerism a simultaneous shift of electrons and a hydrogen atom occurs. Tautomers exist as mixtures of a tautomeric set in solution. In solid form, usually one tautomer predominates. Even though one tautomer may be described, the present invention includes all tautomers of the present compounds.

The invention having now been described by way of written description, those of skill in the art will recognize that the invention can be practiced in a variety of embodiments and that the foregoing description and examples below are for purposes of illustration and not limitation of the claims that follow.

In the specification, the singular forms also include the plural, unless the context clearly dictates otherwise. Unless defined otherwise, all technical and scientific terms used herein have the same meaning as commonly understood by one of ordinary skill in the art to which this invention belongs. In the case of conflict, the present specification will control.

All percentages and ratios used herein, unless otherwise indicated, are by weight.

EXAMPLES

In one embodiment of the invention, melting points were determined with a Buchi 535 electrothermal apparatus and are uncorrected. NMR spectra were obtained with a Bruker AC 200 MHz or 400 MHZ spectrometer and the chemical shifts are reported in parts per million (ppm). The abbreviations used are as follows: s, singlet; bs, broad singlet; d, doublet; dd, double doublet; m, multiplet. Flash column chromatography was performed using Merck silica gel 60 (0.040-0.063 mm) and where indicate using a Biotage SP1 HPCF separation module. 25+M (25 mm×15.0 cm, 40 g), cartridge were used. TLC were carried out on pre-coated TLC plates with silica gel 60 F-254 (Merck). Spots were visualized by staining and warming with phosphomolybdate reagent (5% solution in EtOH).

Example 1

Preparation of 3α,7α,23-trihydroxy-6α-ethyl-24-nor-5β-cholan-23-O-sulfate sodium salt Step 1a: Preparation of Methyl 3α,7α-dihydroxy-6α-ethyl-5β-cholanoate (IIIA)

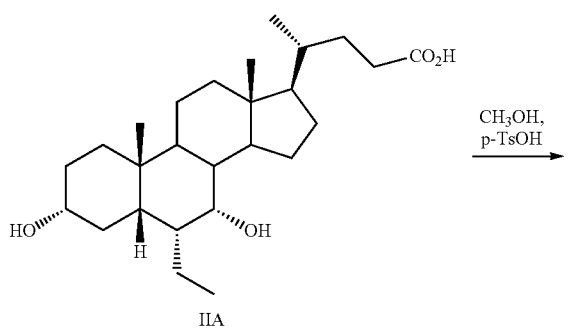

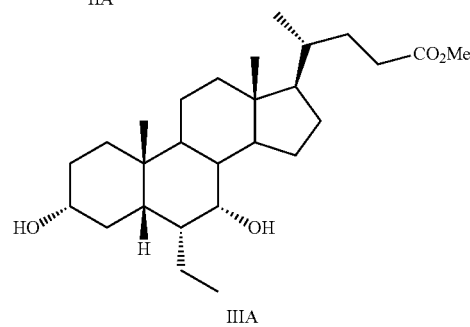

p-Toluenesulfonic acid monohydrate (4 g, 21.03 mmol) was added to a stirring solution of IIA (40 g, 95.1 mmol) in methanol (500 mL) and the reaction mixture was sonicated until complete disappearance of the starting material IIA (checked by TLC), which took approximately 3 h. The solvent was evaporated under vacuum and the resulting residue containing IIIA was dissolved in methylene chloride (500 mL), and washed with a saturated aqueous solution of sodium bicarbonate (3×100 mL), water (100 mL), and brine (100 mL). The organic layer containing IIIA was dried over anhydrous sodium sulfate, and then the solvent was evaporated under vacuum.

Step 2a: Preparation of 3α-acetoxy-7α-hydroxy-6α-ethyl-5β-bisnorcholanyldiphenylethylene (IVA)

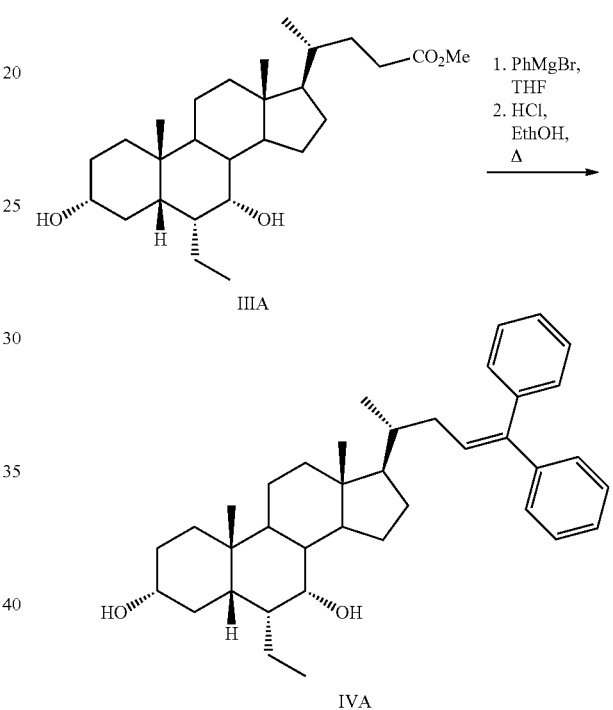

Methyl 3α,7α-dihydroxy-6a-ethyl-5β-cholanoate (IIIA) was dissolved in freshly distilled THF (300 mL), and the resulting mixture was warmed up to 50° C. with stirring under a nitrogen atmosphere. Phenylmagnesiumbromide 1 M in THF (800 mL) was then added dropwise and the resulting reaction mixture was stirred at the same temperature overnight. The reaction mixture was allowed to cool to room temperature and cyclohexane (25 mL) was added. The reaction mixture was filtered and the gum-solid residue was dissolved in a mixture of 3 N hydrochloric acid solution (800 mL) and DCM (200 mL) (CAUTION). The resulting mixture was stirred for 30 min. The organic phase containing IVA was separated, and the aqueous phase was extracted with DCM (2×200 mL). The combined organic layers containing IVA were washed with brine, dried over Na$_2$SO$_4$, and the solvent was evaporated under vacuum. The crude residue containing IVA was taken in DCM (500 mL), washed with a saturated solution of sodium bicarbonate (2×100 mL), water (100 mL), brine (100 mL), dried over anhydrous sodium sulfate and concentrated in vacuo. The residue (containing IVA) obtained was used for the next step without further purification.

Step 3a: Preparation of 3α-acetoxy-7α-hydroxy-6α-ethyl-5β-bisnorcholanyldiphenylethylene (VA)

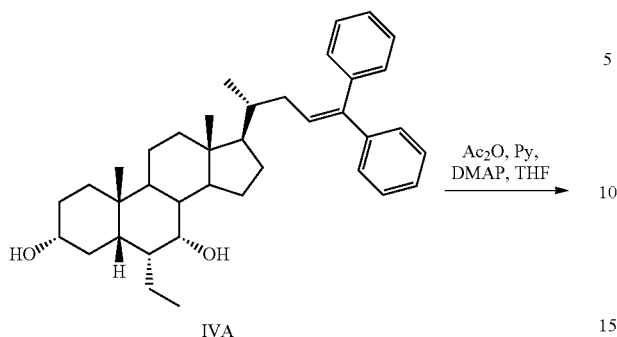

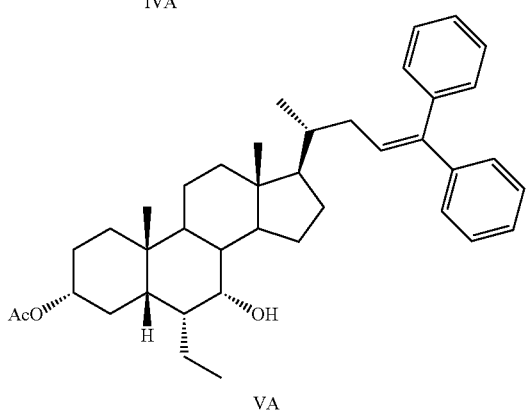

Acetic anhydride (9.92 mL, 105.14 mmol), pyridine (1.6 mL, 19.78 mmol), and 4-dimethylaminopyridine (0.8 g. 6.55 mmol) were added to a stirring solution of 3α,7α-dihydroxy-6α-ethyl-5β-bisnorcholanyldiphenylethylene (IVA) (95.1 mmol) in freshly distilled THF (300 mL). The reaction mixture was kept at room temperature overnight. The reaction mixture was diluted with water (100 mL) and extracted with DCM (3×150 mL). The combined organic layers were washed with brine, dried over anhydrous sodium sulfate and the solvent was evaporated. The residue containing VA was used for the next step without further purification.

$^1$H-NMR (CDCl$_3$) δ 0.66 (3H, s, CH$_3$-18); 0.77 (3H, s, CH$_3$-26); 1.00 (3H, d, CH$_3$-21); 1.20 (3H, s, CH$_3$-19); 1.96 (3H, s, AcO), 2.18-2.31 (1H, m, CH-22); 3.70 (1H, m, CH-7); 4.55 (1H, m, CH-3); 6.11 (1H, dd, J$_1$=6.2 Hz, J$_2$=8.3 Hz; CH-23); 7.14-7.36 (10H, m, Ph).

Step 4a: Preparation of 3α-acetoxy -6α-ethyl-7-keto-24-nor-5β-cholan-23-oic acid (VIA)

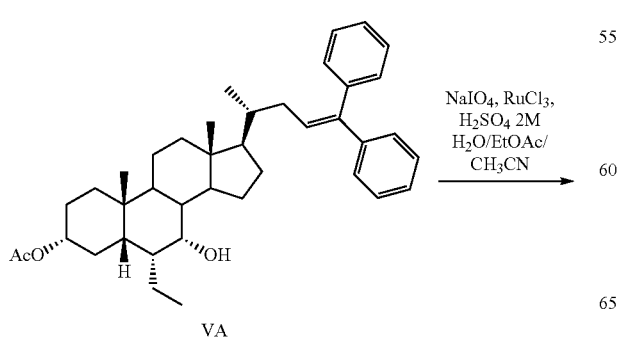

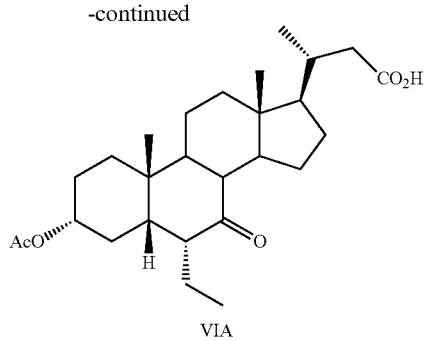

NaIO$_4$ (13.2 g, 61.86 mmol) was stirred in 13 mL of H$_2$O and 2N H$_2$SO$_4$ (1.7 mL). After 15 min., the resulting reaction mixture was cooled to 0° C. and RuCl$_3$ (71.3 mg, 0.34 mmol) was added. The reaction mixture was stirred until the color turned into bright yellow. Ethyl acetate (27 mL) and acetonitrile (20 mL) were added and the resulting reaction mixture was stirred for 5 min. VA (4 g, 6.87 mmol) was added to the reaction mixture at 0° C., and stirred until all VA was consumed (checked by TLC). The reaction mixture was filtered, poured into H$_2$O and extracted with ethyl acetate (3×100 mL). The combined organic layers containing VIA were washed with a saturated solution of Na$_2$S$_2$O$_3$, dried over anhydrous Na$_2$SO$_4$ and concentrated under vacuum. The resulting residue was purified by flash chromatography to give VIA as a white pure solid (2.73 g, 6.11 mmol, 89% yield).

$^1$H-NMR (CDCl$_3$) δ 0.71 (3H, s, CH$_3$-18); 0.86-1.07 (9H, m, CH$_3$-19, CH$_3$-21, C-24); 2.03 (3H, s, AcO); 4.48-4.61 (1H, m, CH-3).

$^{13}$C-NMR (CDCl$_3$) δ 12.0, 12.0, 18.8, 19.5, 21.3, 21.8, 23.4, 24.5, 25.9, 27.7, 28.3, 33.4, 33.8, 35.6, 38.8, 41.2, 42.6, 43.6, 48.9, 49.8, 50.4, 51.9, 54.7, 73.2, 170.6, 179.7, 212.6.

Step 5a: Preparation of 3α-acetoxy-7α-hydroxy-6α-ethyl-24-nor-5β-cholane-23-olo (VIIA)

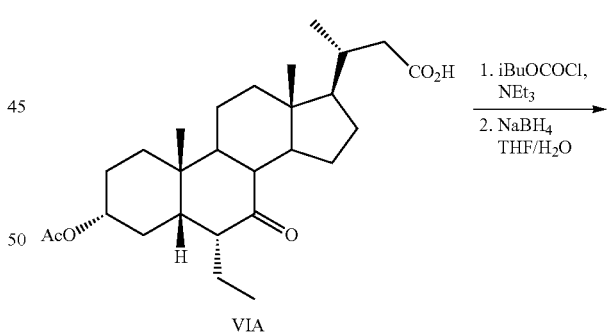

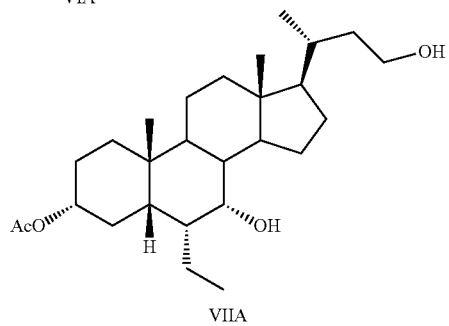

Triethylamine (6.67 mL, 3.36 mmol) was added to a stirring ice-cooled solution of VIA (1 g, 2.24 mmol) and isobutyl chloroformate (3.5 mL, 2.67 mmol) in THF (20 mL). After 1 h, the reaction mixture was filtered under vacuum under an argon atmosphere. The resulting solution was treated with sodium borohydride (847 mg, 22.4 mmol) for 1 h at 0° C., which was added in portions. The reaction mixture was quenched with $H_2O$ (3 mL), stirred for additional 2 h at room temperature, acidified with 3N hydrochloric acid (50 mL) and extract with ethyl acetate (3×15 mL). The combined organic extracts were washed with brine (1×15 mL), dried over anhydrous $Na_2SO_4$, and concentrated under vacuum. VIIA (950 mg) was used for the next step without further purification.

$^1$H-NMR (CDCl$_3$) δ 0.67 (3H, s, CH$_3$-18); 0.86-0.97 (9H, m, CH$_3$-19, CH$_3$-21, CH$_3$-24); 2.03 (3H, s, AcO); 3.72 (3H, m, (2H, m, CH-7, CH$_2$-23); 4.48-4.61 (1H, m, CH-3).

$^{13}$C-NMR (CDCl$_3$) δ 11.6, 11.7, 18.7, 20.7, 21.4, 22.1, 22.9, 23.7, 26.6, 28.4, 29.6, 32.9, 33.2, 35.5, 38.9, 39,.6, 40.0, 41.1, 42.8, 45.0, 50.5, 56.3, 60.8, 70.7, 74.7, 170.7.

Step 6a: Preparation of 3α,7α,23-trihydroxy-6α-ethyl-24-nor-5β-cholan-23-O-sulfate sodium salt (IA)

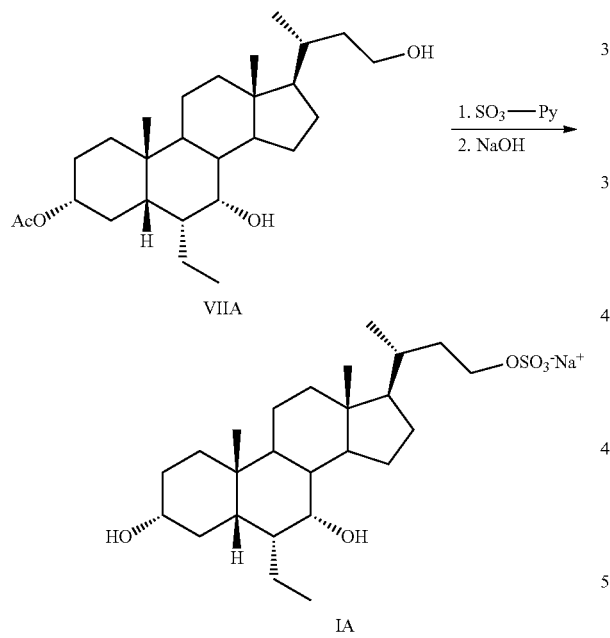

VIIA (8 g, 18.4 mmol) was added to a suspension of sulfur trioxide pyridine complex (3.95 g, 24.84 mmol) in dry pyridine (60 mL) and allowed to reacted at room temperature under nitrogen atmosphere for 24 h. The solvent was evaporated, and the resulting residue was dissolved in methanol (50 mL) and treated with a 10% (w/w) solution of NaOH in MeOH (30 mL). The reaction mixture was refluxed overnight. The solvent was evaporated and the resulting white solid was dissolved in 30 mL of a $H_2O$/MeOH solution (1:1, v:v) and passed through a NaOH activated Dowex resine (h=15 cm, φ=8 cm), eluting first with $H_2O$ (200 mL) and then with a solution of $H_2O$/MeOH (1:1, v:v) (300 mL). The fractions containing IA were evaporated to dryness and the resulting solid was purified via a reverse phase column RP-18 (Lobar C), using as mobile phase a $H_2O$/MeOH mixture. IA (5 g, 56% yield) was obtained as a white pure solid.

m.p.: 183-184° C.

$^1$H-NMR (CD$_3$OD) δ 0.71 (3H, s, CH$_3$-18); 0.89-0.95 (6H, m, CH$_3$-19, CH$_3$ 25); 0.99-1.01 (3H, d, J=6.5 Hz, CH$_3$-21); 3.31 (1H, m, CH-3); 3.65 (1H, m, CH-7); 4.0-4.1 (2H, m, CH$_2$-23).

$^{13}$C-NMR (CD$_3$OD) δ: 73.19, 71.15, 67.20, 57.77, 51.64, 46.95, 43.79, 43.12, 41.54, 41.04, 36.77, 36.62, 36.54, 34.49, 34.41, 34.22, 31.24, 29.34, 24.55, 23.75, 23.48, 21.96, 19.15, 12.19, 12.03.

Example 2

Preparation of Compound VIIA from VA

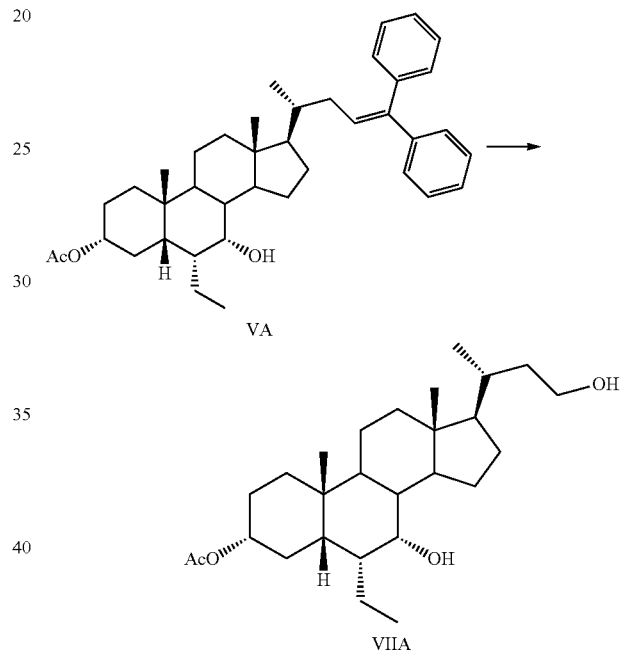

Crude VA (672.0 g, 1.153 mol) was dissolved in dichloromethane (3.0 L). The sample was rotated on the rotavap for about 2 hours until crude VA is completely dissolved. The solution containing VA was transferred to a 3-neck 12 liter round bottom flask equipped with a mechanical stirrer, a bubbler outer, thermocouple, and an $O_3/O_2$ inlet. Dichloromethane (2.376 L) was added to the solution containing VA. The solution containing VA was cooled to about −73° C. to about −78° C. The mixture of $O_3/O_2$ gas (at about 4 psi to about 15 psi or at about 12 psi) was passed through the stirring solution of VA for about 2½ hours until the reaction mixture turned blue/green and TLC confirmed that there was no starting material. The inlet of $O_3/O_2$ gas was shut off, and the $N_2$ was allowed to pass through the reaction mixture for about 40 minutes. To the reaction mixture at about −50° C. to about −75° C. with $N_2$ passing through, NaBH$_4$ (131.0 g, 3.457 mol) and EtOH (1.4 L) were added. The reaction mixture was allowed to stir at about −50° C. to about −55° C. for about 20 minutes, at which time, the reaction mixture was allowed to warm to room temperature and then stirred overnight under $N_2$. TLC was performed to confirm that reaction was complete.

The reaction mixture was cooled to about −5° C. to about −10° C. (or to about −6° C.) over the course of about 1 hour. HCl (1N, 3.1 L) was added slowly to the reaction mixture over the course of about 2½ hour. The pH of the resulting reaction mixture was about 3. The reaction mixture was allowed to warm to room temperature over the course of 1 hour, and then EtOAc (6.5 L) was added. The resulting mixture was stirred well. The organic and the aqueous layers were separated. The aqueous layer was extracted with EtOAc. The organic layers contain VIIA were combined and washed with water (5.5 L), brine (2 times, each at 1.3 L), and then dried over Na$_2$SO$_4$. The organic layer was filtered and the resulting solution was concentrated to dryness to afford 666.0 g of crude VIIA.

Compound VIIA can be purified according to the procedure described below. Compound VIIA obtained above was dissolved in dichloromethane (2.0 L, rinsed with 0.6 L). A Biotage column was flushed with THF (3 times, 20 L each). The Biotage column was confirmed to be clean by TLC. The Biotage column was equilibrated with hexanes (20 L). VIIA in dichloromethane was poured onto column. The column was first eluted with 100 L of hexanes:EtOAc (9:1), then 200 L of hexanes: EtOAc (8.5:1.5), and then 100 L of hexanes: EtOAc (7:3). The fractions containing purified VIIA were concentrated to dryness to afford 255.0 g (50.9% yield from VA).

Figure 2:
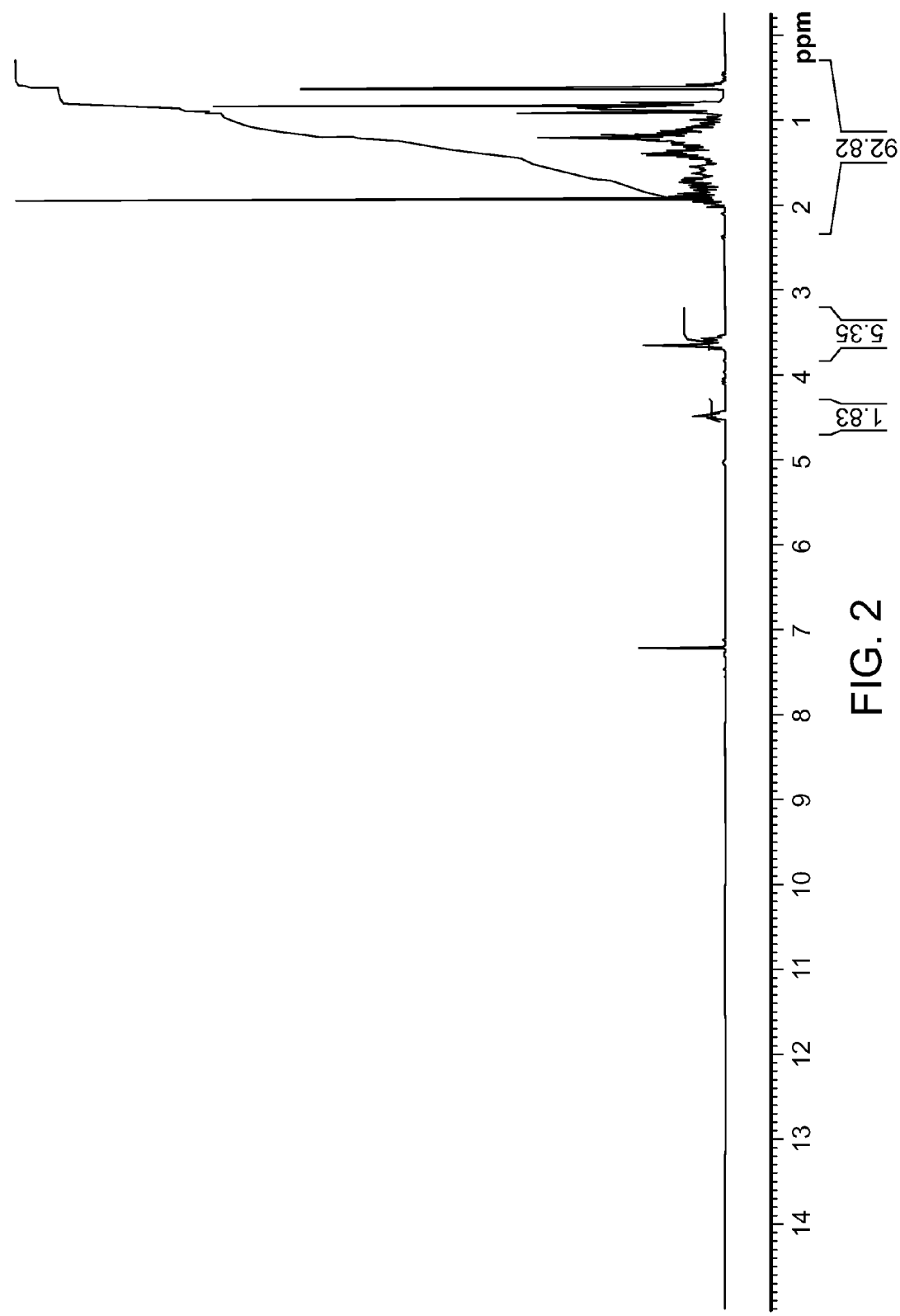
FIG. 2: $^1$H NMR spectrum of compound VIIA obtained from Example 2.

Compound VIIA from the first purification can be purified again according to the following procedures. The Biotage column was flushed with THF until TLC confirmed that it is clean. Compound VIIA (241.5 g) was dissolved in dichloromethane (0.480 L, rinsed with 0.480 L) and poured onto the column. The column was eluted with 50 L of hexanes: EtOAc (9:1), 50 L of hexanes:EtOAc (8.5:1.5), 100 L of hexanes:EtOAc (8:2), and then 200 L of hexanes:EtOAc (7:3). The fractions containing pure VIIA were concentrated to dryness to afford 169.0 g. See FIG. 1 for a chromatogram of HPLC of purified VIIA and FIG. 2 for $^1$H NMR spectrum of purified VIIA.

Example 3

Preparation of 3α,7α,23-trihydroxy-6α-ethyl-24-nor-5β-cholan-23-O-sulfate sodium salt Step Aa: 3α,7α-Diacetoxy-6α-ethyl-5β-bisnorcholanyldiphenylethylene (3)

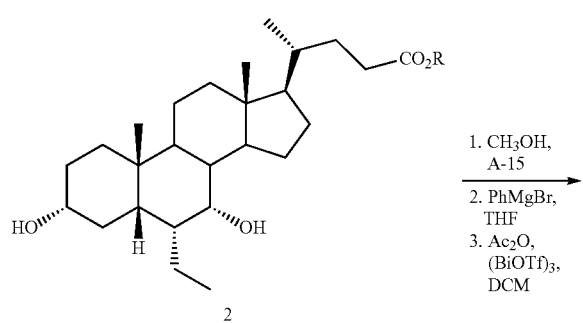

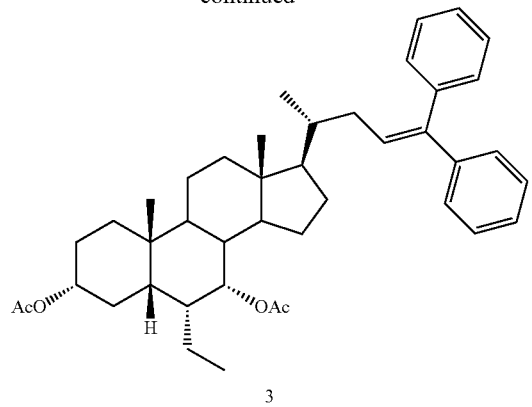

A solution of compound 2 (1 g, 2.4 mmol) and Amberlist A-15 in methanol (20 mL) was reacted until the complete disappearance of the starting material (checked by TLC) (4 h). The reaction mixture was filtered, A-15 was washed with MeOH, and the solvent removed under vacuum. The methyl ester thus formed (1.1 g) was dissolved in freshly distilled THF (15 mL), and the mixture was warmed up to 50° C. under magnetic stirring and nitrogen atmosphere. Phenylmagnesiumbromide 3 M in Et$_2$O (3.83 mL, 12 mmol) was then added dropwise and the resulting mixture was stirred at the same temperature for additional 4 h. The solution was allowed to cool at room temperature and cyclohexane (25 mL) was added. The resulting suspension was filtered and the gum-solid residue was dissolved in a mixture of 3 N hydrochloric solution (50 mL) and dichloromethane (25 mL). The mixture was stirred for 30 min. The organic phase was separated, and the aqueous phase was extracted with dichloromethane (3×25 mL). The combined organic layers were washed with brine, dried over Na$_2$SO$_4$, and concentrated. The crude reaction mixture was redissolved in dichloromethane (30 mL) and reacted with acetic anhydride (0.72 mL, 7.6 mmol) in the presence of Bi(OTf)$_3$ (15 mg, 0.115 mmol) at room temperature for 3 h. The mixture was filtered on Celite®, treated with NaOH 1 M in water (50 mL) and extracted with dichloromethane (3×15 mL). The combined organic layers were washed with brine, dried over anhydride sodium sulphate and concentrated. After filtration on a silica gel pad, compound 3 was obtained as white solid in 92% yield (1.15 g).

$^1$H-NMR (CDCl$_3$) δ 0.64 (3H, s, CH$_3$-18); 0.88 (3H, t, CH$_3$-26); 0.93 (3H, s, CH$_3$-19); 1.01 (3H, d, CH$_3$-21); 2.03 (3H, s, AcO), 2.06 (3H, s, AcO), 2.18-2.31 (1H, m, CH-22); 4.58 (1H, m, CH-3); 5.09 (1H, m, CH-7); 6.11 (1H, dd, J$_1$=6.2 Hz, J$_2$=8.3 Hz; CH-23); 6.75-7.37 (10H, m, Ph).

$^{13}$C-NMR (CDCl$_3$) δ 11.3, 11.4, 18.7, 20.3, 21.0, 21.2, 21.9, 22.7, 23.6, 26.4, 27.8, 28.6, 33.8, 34.8, 35.1, 35.6, 36.6, 38.5, 39.0, 41.0, 42.6, 44.6, 50.2, 55.5, 72.8, 74.2, 126.4, 126.7, 127.8, 128.6, 129.6, 140.1, 141.9, 142.6, 170.1, 170.3.

Step Ba: 3α,7α-Diacetoxy-6α-ethyl-24-nor-5β-cholan-23-oic acid (4)

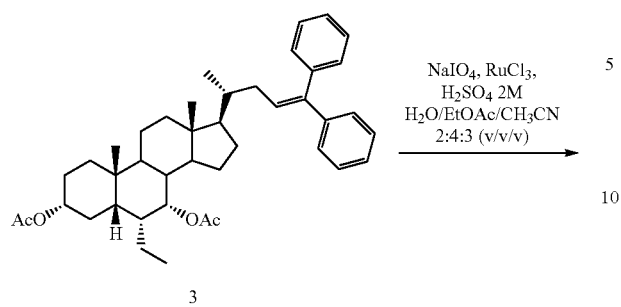

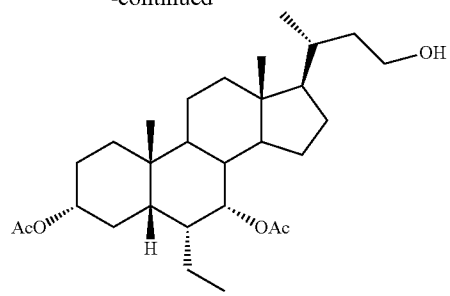

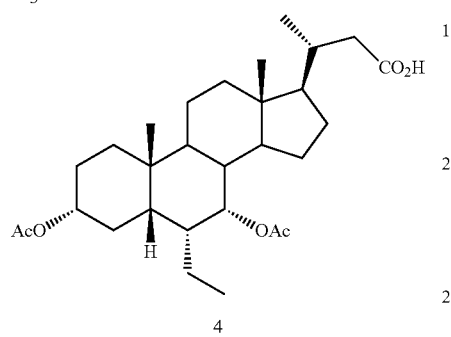

4

NaIO$_4$ (1.32 g, 6.186 mmol) was stirred in 1.3 mL of H$_2$O and 2 N H$_2$SO$_4$ (0.17 mL). After 15 min., the solution was cooled at 0° C. and RuCl$_3$ (7.13 mg, 0.034 mmol) was added. This mixture was stirred until the colour turned bright yellow. Ethyl acetate (2.7 mL) and acetonitrile (2.0 mL) were added and the resulting mixture was stirred for 5 min. Compound 3 (400 mg, 0.687 mmol) was added at 0° C., and the mixture was stirred until compound 2 starting material was consumed. The mixture was filtered off, poured onto H$_2$O and extracted with ethyl acetate (3×25 mL). The combined organic layers were washed with saturated Na$_2$S$_2$O$_3$ solution, dried over Na$_2$SO$_4$ and concentrate under reduced pressure. The resulting residue was purified by flash chromatography to give compound 4 (2.7 g, 6.1 mmol, 89% yield).

$^1$H-NMR (CDCl$_3$) δ 0.70 (3H, s, CH$_3$-18); 0.88 (3H, t, CH$_3$-26); 0.96 (3H, s, CH$_3$-19); 1.04 (3H, d, CH$_3$-21); 2.06 (3H, s, AcO), 2.09 (3H, s, AcO), 2.47 (1H, dd, CH-22); 4.54-4.62 (1H, m, CH-3); 5.12 (1H, s, CH-7). $^{13}$C-NMR (CDCl$_3$) δ 11.2, 11.3, 19.1, 20.2, 21.1, 21.8, 22.6, 23.4, 27.7, 28.6, 33.6, 34.0, 35.5, 38.9, 40.0, 41.1, 43.0, 45.0, 50.6, 55.7, 73.1, 74.6, 170.5, 170.7, 177.9.

Step C: 3α,7α-Diacetoxy -6α-ethyl-24-nor-5β-cholane-23-olo (5)

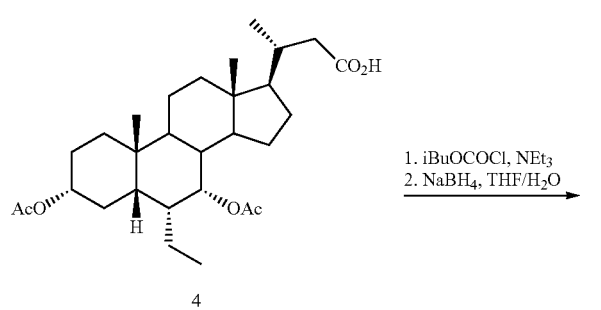

A stirred ice-cooled solution of compound 4 (300 mg, 0.6 mmol), isobutyl chloroformate (0.72 mmol) and triethylamine (0.78 mmol) in freshly distilled THF (20 mL) was reacted for 1 h. The reaction mixture was then filtered under vacuum in argon atmosphere. The crude material was cooled at 0° C. and sodium borohydride (1.27 g 33.6 mmol) was added in portions. The resulting mixture was stirred for 1 h and H$_2$O (3 mL) was then added. The reaction mixture was stirred for additional 2 h at room temperature, and then it was acidified with 3 N hydrochloric acid (50 mL) and extracted with ethyl acetate (3×15 mL). The combined organic extracts were washed with brine (1×15 mL), dried over Na$_2$SO$_4$, and concentrate under reduced pressure to give compound 5 (300 mg), which was used for the next step without further purification.

$^1$H-NMR (CDCl$_3$) δ 0.63 (3H, s, CH$_3$-18); 0.86-0.97 (9H, m, CH$_3$-19, CH$_3$-21, CH$_3$-25); 2.00 (3H, s, AcO); 2.00 (3H, s, AcO); 3.57-3.83 (2H, m, CH$_2$-23); 4.54-4.62 (1H, m, CH-3); 5.12 (1H, s, CH-7). $^{13}$C-NMR (CDCl$_3$) δ1.6, 11.7, 18.8, 20.7, 21.3, 21.4,5, 22.2, 23.0, 23.8, 26.8, 28.2, 29.0, 32.9, 34.1, 35.1, 35.5, 38.9, 39.4, 41.1, 42.9, 45.0, 50.5, 56.3, 60.8, 73.2, 74.5, 170.4, 170.6.

Step D: 3α,7α,23-trihydroxy-6α-ethyl-24-nor-5β-cholan-23-O-sulfate sodium salt (IA)

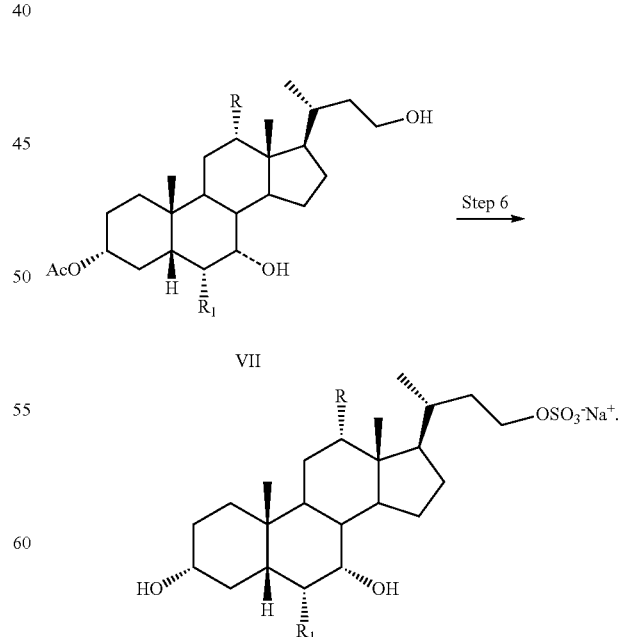

To a suspension of sulfur trioxide pyridine complex (190 mg, 1.2 mmol) in dry pyridine (2 mL), compound 5 was added and the resulting mixture was stirred under nitrogen atmosphere for 24 h. The solvent was the removed and the residue was dissolved in methanol (5 mL) and refluxed overnight with a 10% (w/w) solution of NaOH in MeOH (7 mL). The solvent was evaporated and the resulting white solid was dissolved in 5 mL of a solution of H$_2$O/MeOH (1:1, v/v) and passed through a NaOH activated Dowex resin, eluting first with H$_2$O (40 mL) and then with a H$_2$O/MeOH (1:1, v/v) (30 mL). The fractions containing the compounds were evaporated to dryness and the resulting solid has been purified over a reverse phase column RP-18 (Lobar C), using a solution of H$_2$O/MeOH as mobile phase. Compound IA was obtained in 55% yield. m.p.: 183-184° C. $^1$H-NMR (CD$_3$OD) δ 0.71 (3H, s, CH$_3$-18); 0.89-0.95 (6H, m, CH$_3$-19, CH$_3$-25); 0.99-1.01 (3H, d, J=6.5 Hz, CH$_3$-21); 3.31 (1H, m, CH-3); 3.65 (1H, m, CH-7); 4.0-4.1 (2H, m, CH$_2$-23). $^{13}$C-NMR (CD$_3$OD) δ: 73.19, 71.15, 67.20, 57.77, 51.64, 46.95, 43.79, 43.12, 41.54, 41.04, 36.77, 36.62, 36.54, 34.49, 34.41, 34.22, 31.24, 29.34, 24.55, 23.75, 23.48, 21.96, 19.15, 12.19, 12.03.

Equivalents

Those skilled in the art will recognize, or be able to ascertain using no more than routine experimentation, many equivalents to the specific embodiments and methods described herein. Such equivalents are intended to be encompassed by the scope of the present invention.

All patents, patent applications, and literature references cited herein are hereby expressly incorporated by reference.

The invention claimed is:

1. The process for preparing a compound of formula I:

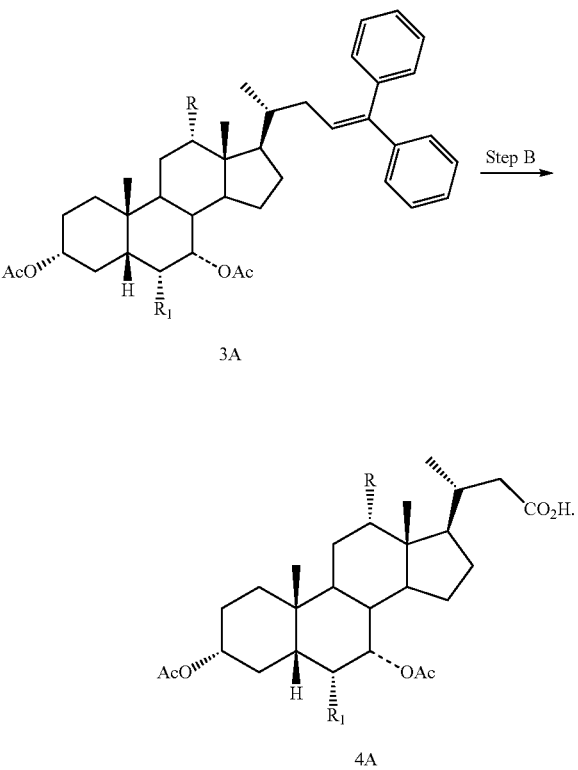

or a pharmaceutically acceptable salt or solvate thereof, wherein
 the dashed bond (----) at position 7 indicates that the substituent is in a α or β sterochemistry;
 R is hydrogen or hydroxy; and
 R$_1$ is hydrogen or C$_1$-C$_6$ alkyl;
comprising the step of converting a compound of formula 3A to a compound of formula 4A:

wherein Step B comprises reacting a compound of formula 3A with RuCl$_3$, NaIO$_4$, and an acid to form a compound of formula 4A.

2. The process of claim 1, wherein R$_1$ is ethyl.

3. The process of claim 1, wherein the compound is selected from

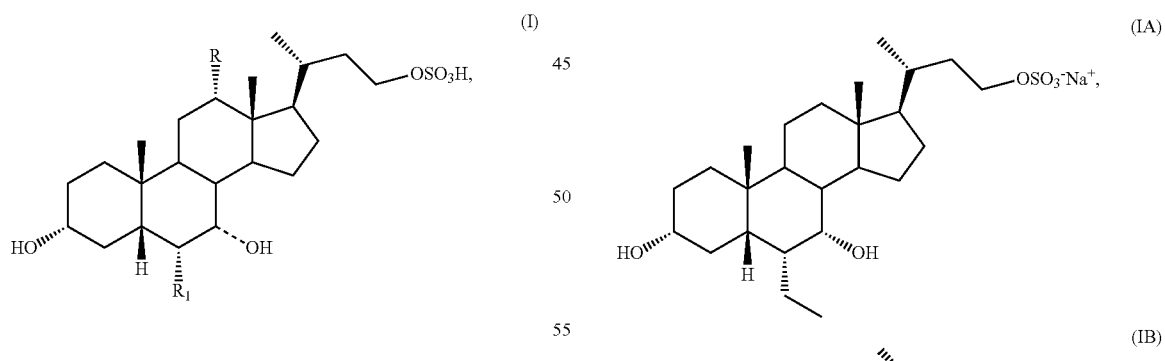

(IC)
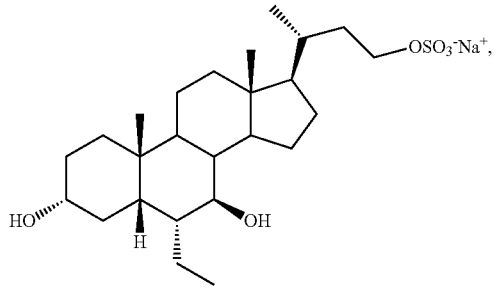
(ICC)
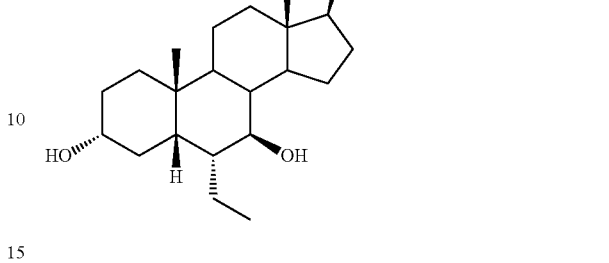
(ID)
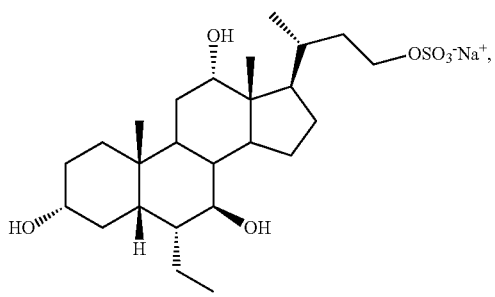
(IDD)
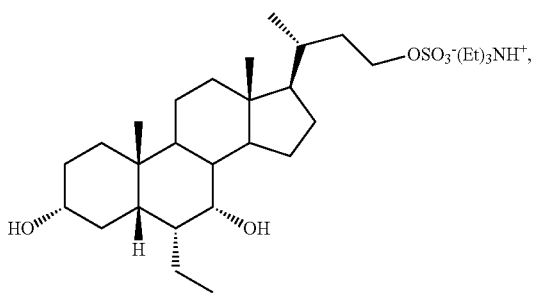
4. The process of claim 1, further comprising the step of Step D, wherein Step D comprises reacting a compound of formula 5A with a sulfonating agent to form a compound of formula I-Na:
(IAA)
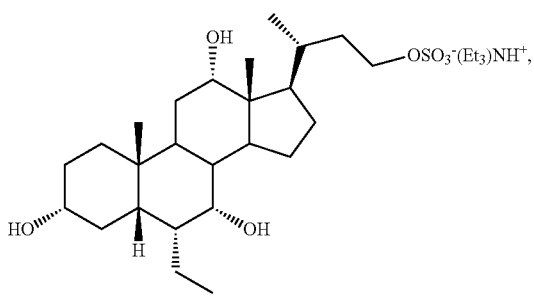
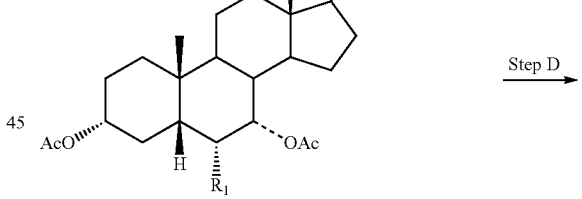
(IBB)
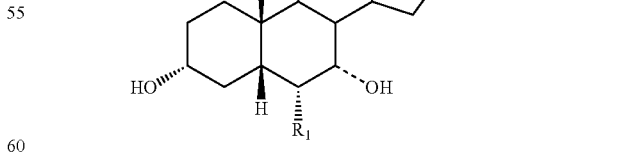
5. The process of claim 1, further comprising the step of Step C, wherein Step C comprises reacting a compound of formula 4A with a reducing agent to form a compound of formula 5A:

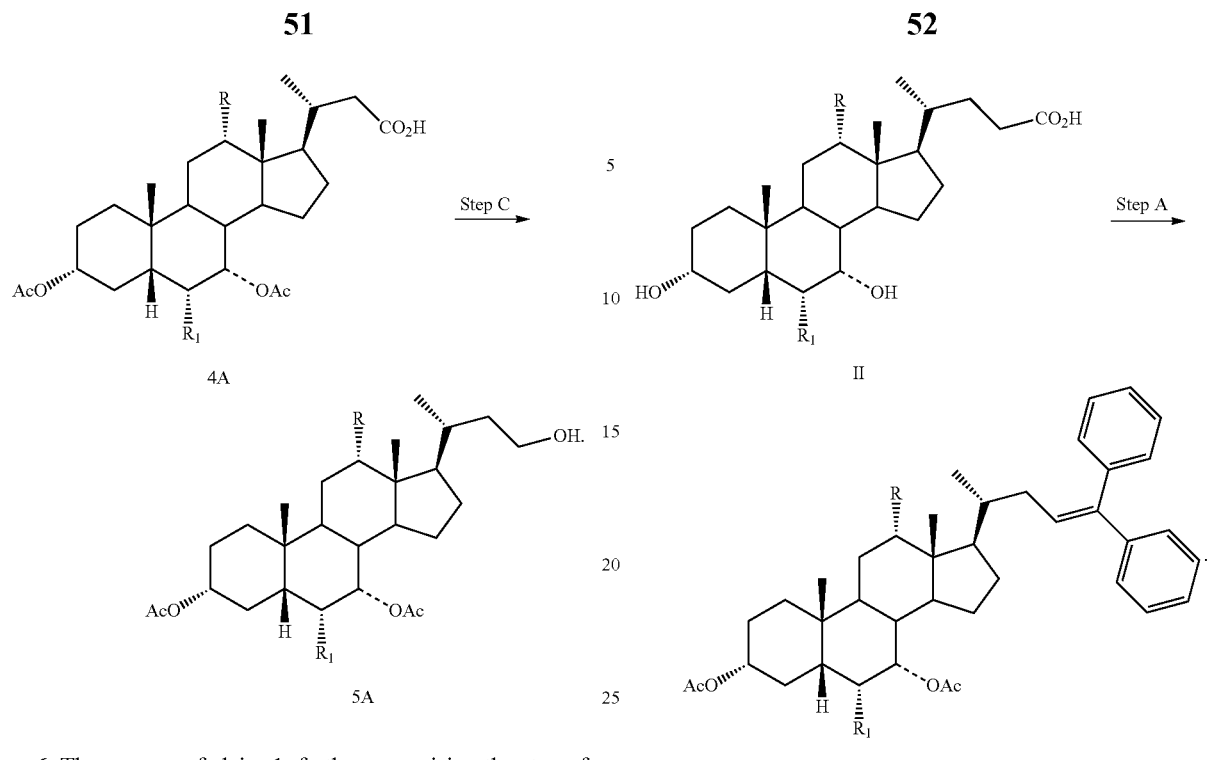
6. The process of claim 1, further comprising the step of Step A, wherein Step A comprises a Grignard reaction and protection of the hydroxyl group to form a compound of formula 3A:
* * * * *